(12) United States Patent
Paul et al.

(10) Patent No.: US 9,839,745 B2
(45) Date of Patent: Dec. 12, 2017

(54) DEVICE AND METHOD FOR DISPENSING FLUID FROM AN INFUSION PUMP

(71) Applicant: Trividia Healthcare Systems, LLC, Fort Lauderdale, FL (US)

(72) Inventors: Patrick J. Paul, Boca Raton, FL (US); Edward D. Arguello, Weston, FL (US); Alexandre A. N. Baptista, Plantation, FL (US)

(73) Assignee: Trividia Healthcare Systems, LLC, Fort Lauderdale, FL (US)

( * ) Notice: Subject to any disclaimer, the term of this patent is extended or adjusted under 35 U.S.C. 154(b) by 977 days.

(21) Appl. No.: 13/934,793

(22) Filed: Jul. 3, 2013

(65) Prior Publication Data

US 2014/0035604 A1 Feb. 6, 2014

Related U.S. Application Data

(60) Provisional application No. 61/677,624, filed on Jul. 31, 2012.

(51) Int. Cl.
*A61M 5/142* (2006.01)
*A61M 5/168* (2006.01)
(Continued)

(52) U.S. Cl.
CPC .... *A61M 5/14248* (2013.01); *A61M 5/16831* (2013.01); *A61M 5/31511* (2013.01); *G01F 23/22* (2013.01); *A61M 2005/31518* (2013.01)

(58) Field of Classification Search
CPC .... A61M 5/31511; A61M 2005/31518; A61M 5/16831; A61M 5/14248; G01F 23/22
See application file for complete search history.

(56) References Cited

U.S. PATENT DOCUMENTS 3,965,802 A * 6/1976 Jacobs .................. B66F 13/005
187/272
4,525,164 A * 6/1985 Loeb ................. A61M 5/14244
128/DIG. 12
(Continued)

FOREIGN PATENT DOCUMENTS

EP 2438938 A1 4/2012
JP H07-308377 11/1995
(Continued)

OTHER PUBLICATIONS

International Search Report and Written Opinion for International Application No. PCT/US2013/049258 dated Sep. 19, 2013, 13 pages.

*Primary Examiner* — Bhisma Mehta
*Assistant Examiner* — Hamza Darb
(74) *Attorney, Agent, or Firm* — Greenberg Traurig, LLP; David J. Dykeman; Roman Fayerberg

(57) ABSTRACT

The present disclosure is directed towards a compact, modular infusion pump and a delivery mechanism for accurate dispensing of very small amounts of medication. The infusion pump comprises a tubular, curved medication reservoir, and a flexible, one-piece drive train configured to push very small amounts of medication out of the medication reservoir. A method of measuring a level of medication inside the medication reservoir or cross-checking the accuracy of medication delivery is also described.

36 Claims, 28 Drawing Sheets

(51) Int. Cl.
  *G01F 23/22* (2006.01)
  *A61M 5/315* (2006.01)

(56) References Cited

U.S. PATENT DOCUMENTS

| | | | | |
|---|---|---|---|---|
| 5,261,882 A * | 11/1993 | Sealfon | ............... | A61M 5/1454 |
| | | | | 128/DIG. 12 |
| 7,220,248 B2 * | 5/2007 | Mernoe | ............. | A61M 5/14244 |
| | | | | 604/218 |
| 7,896,197 B2 * | 3/2011 | Furey | ................... | B67D 1/0012 |
| | | | | 222/64 |
| 2002/0045861 A1 * | 4/2002 | Tribe | ............... | A61M 5/14546 |
| | | | | 604/154 |
| 2002/0087125 A1 * | 7/2002 | Pokorney | ........... | A61M 5/31511 |
| | | | | 604/227 |
| 2007/0154336 A1 * | 7/2007 | Miyazaki | .......... | A61M 5/14228 |
| | | | | 417/474 |
| 2007/0179444 A1 * | 8/2007 | Causey | ............ | A61M 5/14244 |
| | | | | 604/131 |
| 2008/0077081 A1 * | 3/2008 | Mounce | .............. | A61M 5/1413 |
| | | | | 604/67 |
| 2012/0259282 A1 * | 10/2012 | Alderete, Jr. | ....... | A61M 5/5086 |
| | | | | 604/131 |

FOREIGN PATENT DOCUMENTS

| | | |
|---|---|---|
| JP | 2001-187138 | 10/2001 |
| JP | 2004-275466 | 10/2004 |
| WO | WO 82/03556 A1 | 10/1982 |
| WO | 1998-001173 | 1/1998 |
| WO | 2001-078812 | 10/2001 |
| WO | WO 2008/024812 A2 | 2/2008 |
| WO | 2011-081980 | 7/2011 |

* cited by examiner

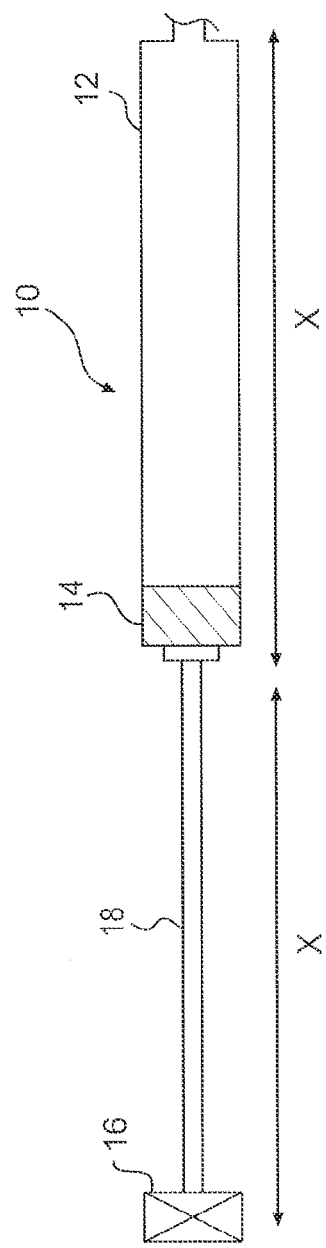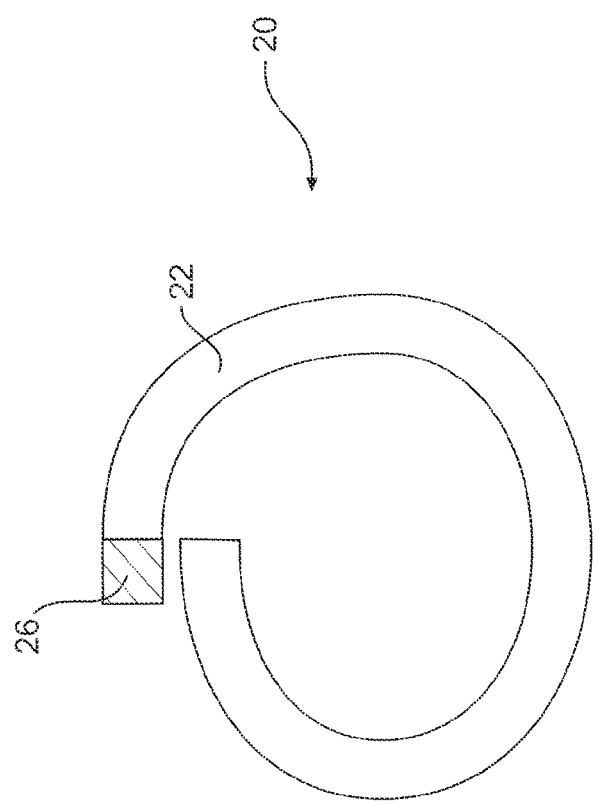
FIG. 1
FIG. 2

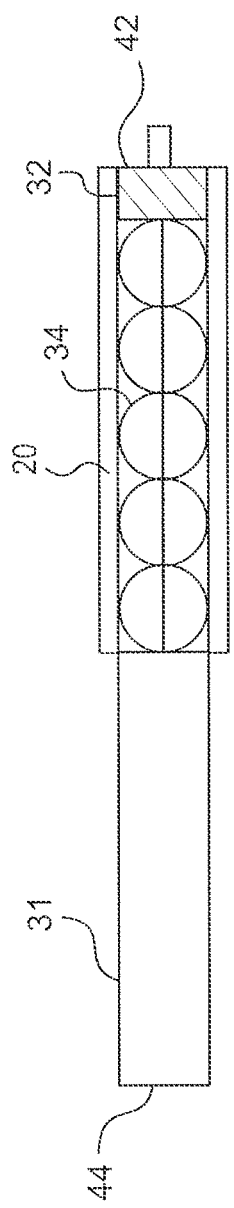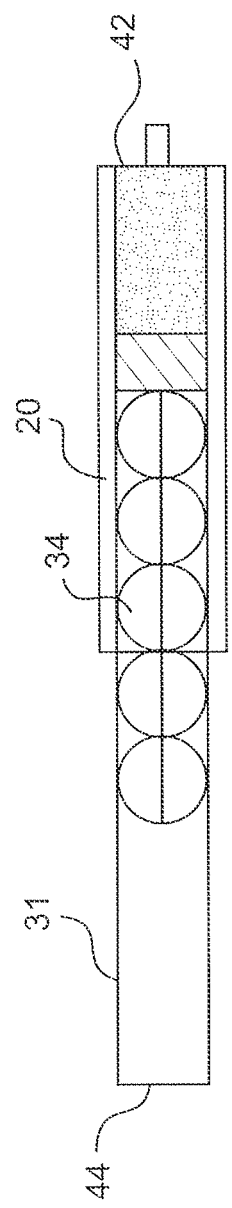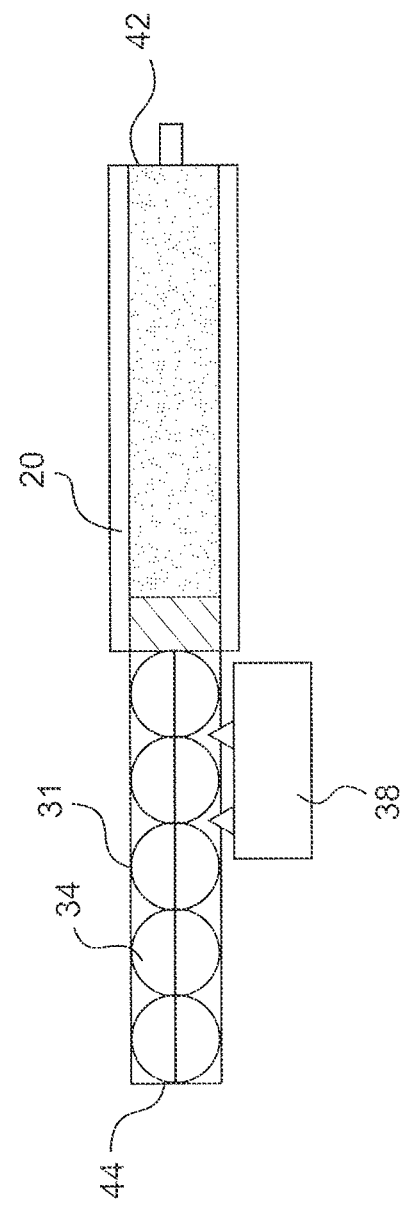

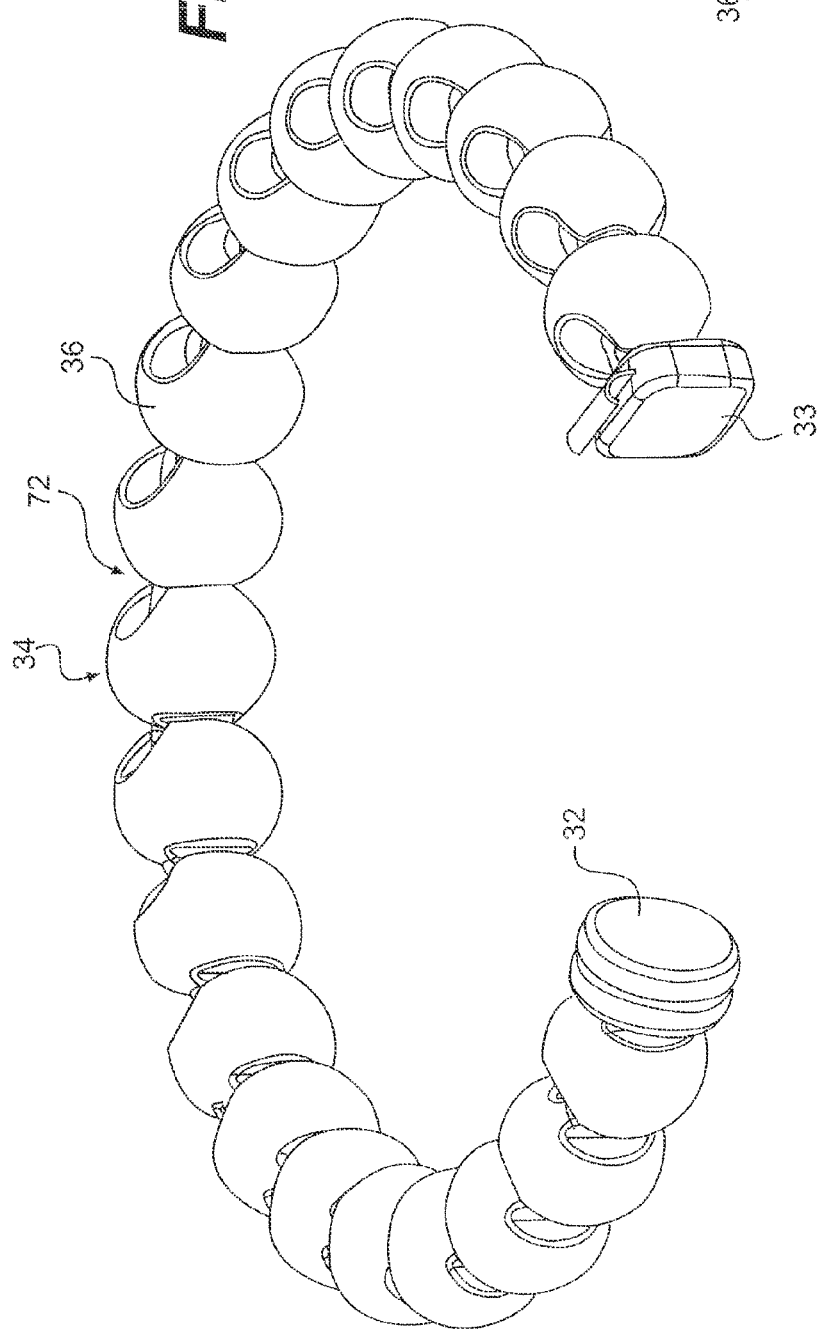
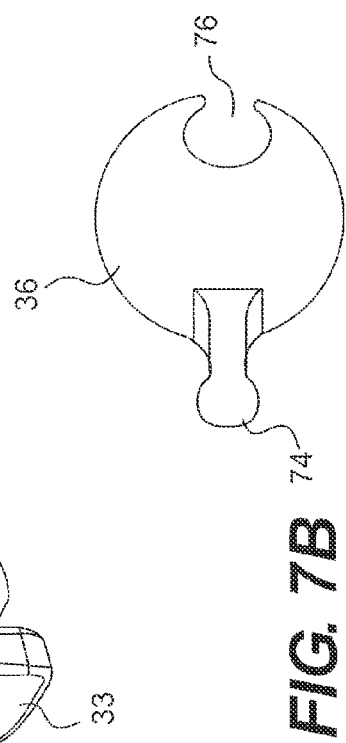

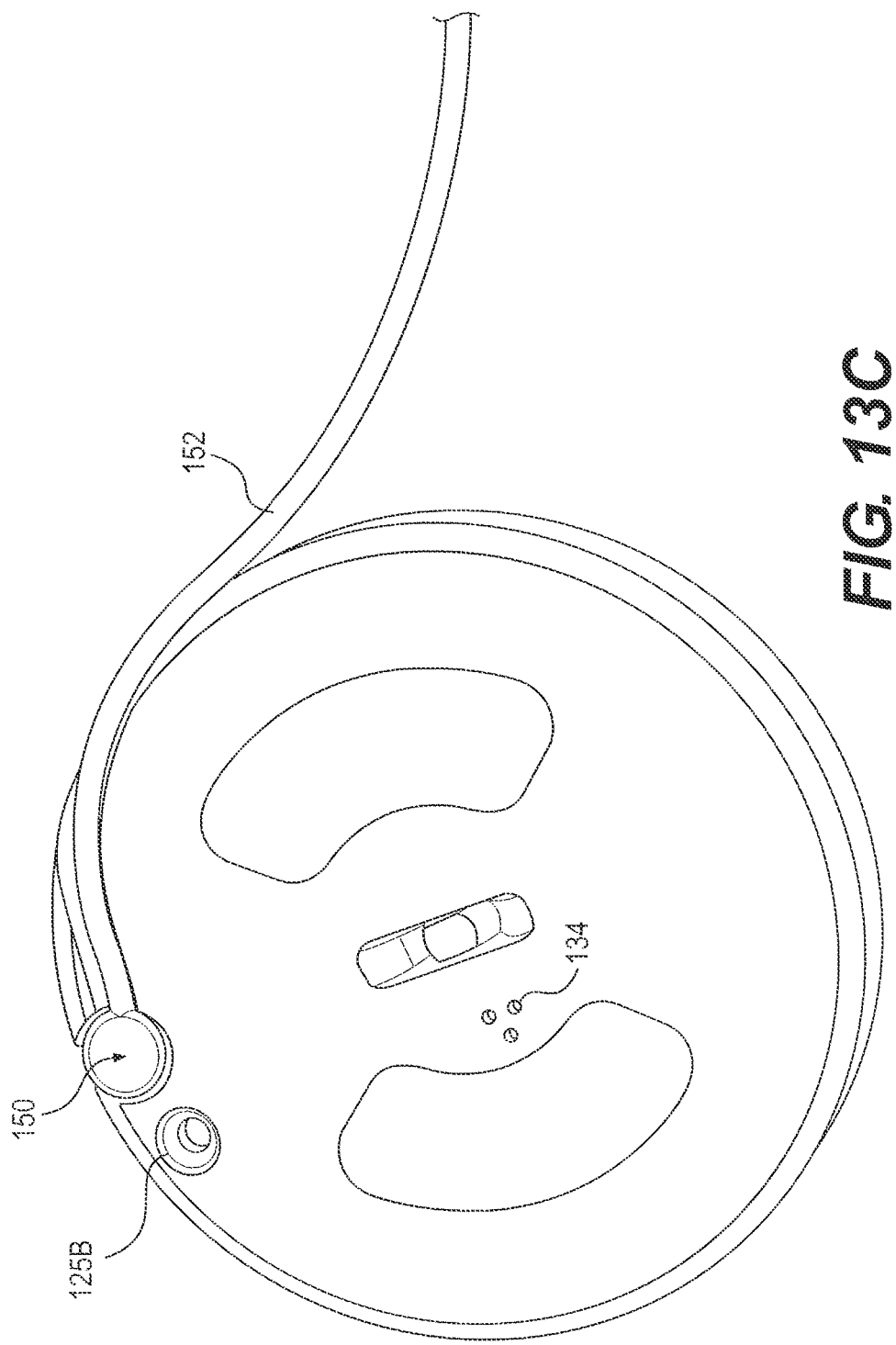

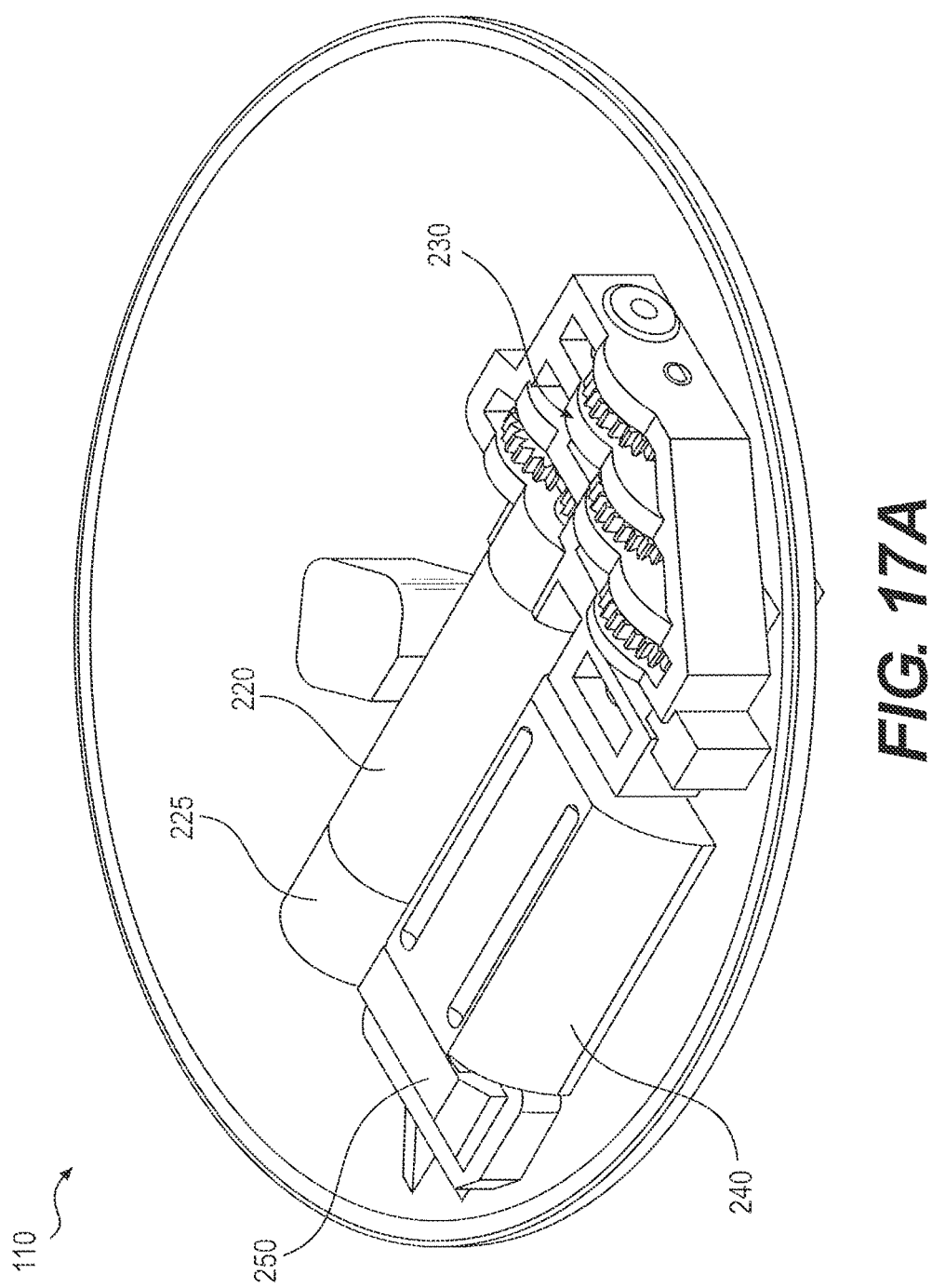

DEVICE AND METHOD FOR DISPENSING FLUID FROM AN INFUSION PUMP

This application claims priority to U.S. Provisional Application No. 61/677,624, filed Jul. 31, 2012, which is incorporated herein by reference in its entirety.

This invention relates to the field of medical infusion pumps, and in particular, to a system and method for accurate delivery of very small amounts of fluidic medication from an infusion pump.

An infusion pump, such as a patch-type infusion pump or a traditional portable infusion pump, represents an active drug delivery system, usually having a fluidic reservoir, an onboard energy source, a pump, a delivery cannula, and a control unit all integrated into a single device. Patch pumps in particular are configured to be either entirely disposable or semi-disposable where parts such as the drug reservoir can be detached and replaced when empty. More characteristically, patch pumps differ from earlier portable infusion pumps in that they do not have any external tubes (infusion sets) and they attach directly to the skin and deliver drugs transdermally or subcutaneously via a cannula. Most infusion pumps also have wireless communications capability, allowing them to communicate wirelessly with a remote controller used for setting rates, delivering boluses, tracking delivery, etc. Some infusion pumps are completely self-contained and have a control capability built into the device. Infusion pumps are designed for basal and bolus drug doses set at fixed and variable rates. Infusion pumps, and in particular the patch-type infusion pumps, can be used as wearable drug delivery devices for continuous delivery of medication at various rates or volumes. For example, infusion pumps can be used for round-the-clock insulin delivery for diabetes management. There are profound performance and design challenges involved in developing a successful infusion pump configuration for continuous drug delivery regimens. For pediatric use in particular, infusion pump systems for continuous drug administration must have precise control over the amount of drug delivered and the rate of delivery at any time, in addition to their miniature size. Further, an infusion pump must be as unobtrusive to the wearer as possible, and preferably also be inconspicuous to others. Compact, ergonomic form factors, while desirable from a wearer lifestyle perspective, cannot compromise delivery control. Precise control is all the more challenging to achieve in a compact form factor when delivery rates are very small, as is typical in the case of basal insulin delivery.

The present disclosure is directed towards a compact, modular infusion pump and a delivery mechanism for accurate dispensing of very small amounts of medication. The devices and methods of the present disclosure can be employed with all types of infusion pumps, including, but not limited to, patch-type infusion pumps.

An exemplary embodiment of the present disclosure is a modular infusion pump for dispensing a fluid, the pump comprising a reservoir module and a control module. The reservoir module comprises a curved reservoir containing the fluid, the curved reservoir having a proximal end and a distal end, and a flexible drive train configured to slidably fit within the curved reservoir and to expel the fluid through the proximal end of the reservoir. The control module comprises an electric motor, a drive shaft, and a lead screw, wherein the lead screw is configured to mechanically engage the drive train when the reservoir module is coupled to the control module.

It is to be understood that both the foregoing general description and the following detailed description are exemplary and explanatory only and are not restrictive of the invention, as claimed.

BRIEF DESCRIPTION OF DRAWINGS

The accompanying drawings, which are incorporated in and constitute a part of this specification, illustrate embodiments of the invention and together with the description, serve to explain the principles of the various aspects of the invention.

FIG. 1 illustrates a prior art syringe-type reservoir having a rigid, rectilinear plunger rod;

FIG. 2 illustrates a long, curved medication reservoir for use in a patch pump, in accordance with exemplary embodiments of the present disclosure;

FIGS. 4A-4C illustrate a sequential method of filling a reservoir with medication, in accordance with exemplary embodiments of the present disclosure;

FIG. 7A illustrates another alternative drive train having an assembly of interconnected ball segments, in accordance with exemplary embodiments of the present disclosure;

FIG. 7B illustrates a top view of a ball segment of the drive train embodiment depicted in FIG. 7A;

FIGS. 13A-13E illustrate the underside of the reservoir module of an exemplary infusion pump embodiment having separate medication output port and fill port;

FIGS. 17A-17C illustrate the output mechanism of the control module, in accordance with exemplary embodiments of the present disclosure.

DESCRIPTION OF ILLUSTRATIVE EMBODIMENTS

Figure 3A:
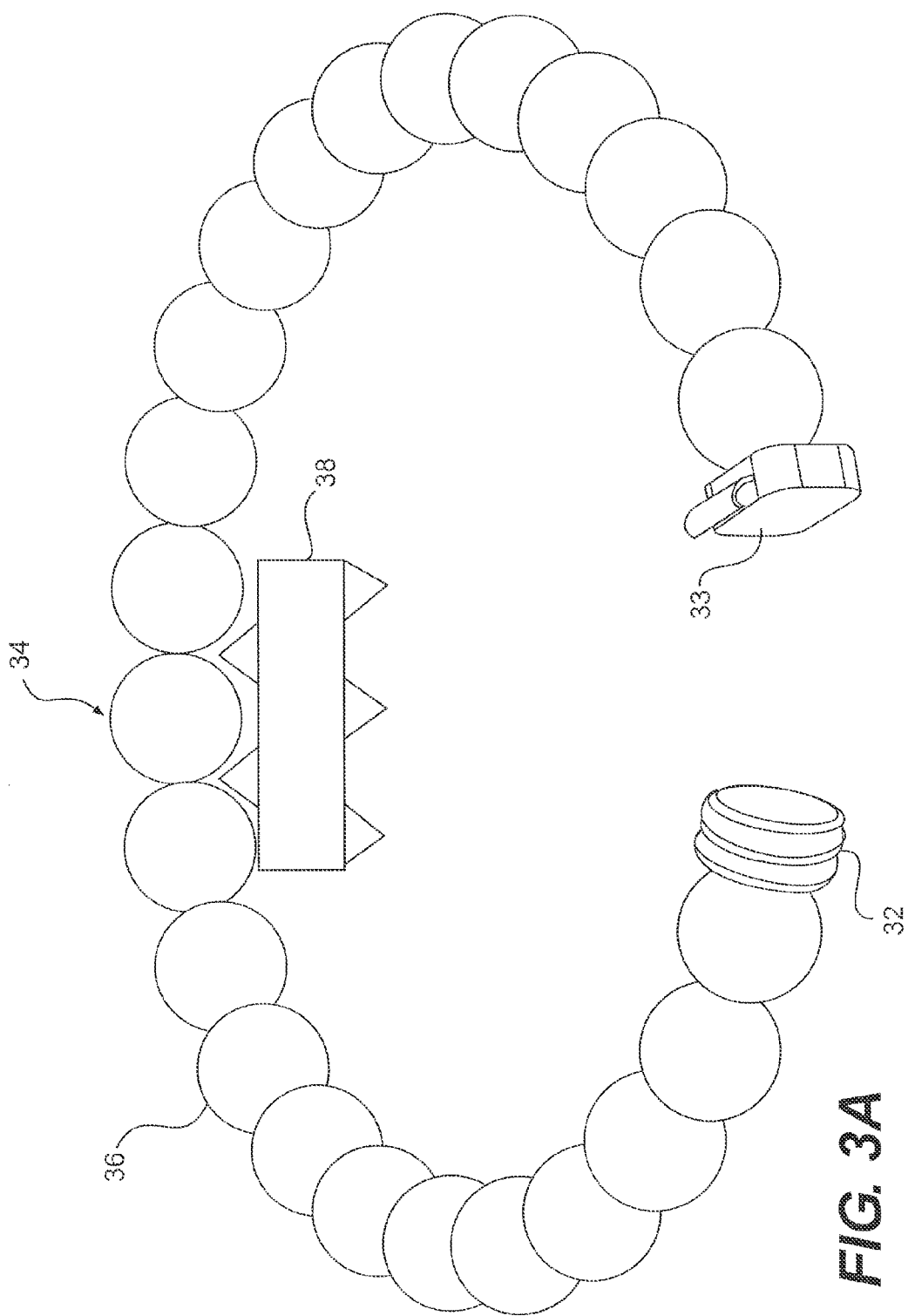
FIG. 3A illustrates a flexible plunger rod comprising a drive train having an assembly of interconnected ball segments, in accordance with exemplary embodiments of the present disclosure.

Reference will now be made in detail to certain embodiments consistent with the present disclosure, examples of which are illustrated in the accompanying drawings. Wherever possible, the same reference numbers will be used throughout the drawings to refer to the same or like parts. It is to be understood that the devices and methods of the present disclosure can be employed with all types of infusion pumps for fluidic medication delivery.

A first aspect of the present disclosure is a method of implementing an infusion pump capable of delivering very small amounts of medication. In exemplary embodiments of the present disclosure, precise delivery of very small amounts of fluidic medication is achieved by using a medication reservoir that is sized as a long syringe having a small cross-section. In illustrative embodiments, the medication reservoir is in the form of a long, narrow tube. The tube houses a plunger that is sized to fit snugly, but slidably within the tube. In exemplary embodiments, the tube has a circular cross-section, although any other cross-section (e.g., oval, etc.) that allows the plunger to fit securely within the tube and provide a seal can be used. The plunger is configured to slide along the inner walls of the tube allowing the reservoir to be filled with fluidic medication and to expel the medication through an opening at a proximal end (i.e., the end of the tube that is proximate a medication delivery port) of the reservoir.

Delivery of small volumes of fluid is mechanically more precise when a long, narrow reservoir is employed, because a smaller cross-section translates to a smaller volume of fluid expelled for each unit of forward movement ("step size") of a plunger. For very small basal deliveries, e.g. pediatric insulin basal rate of 250 nL/hour, very precise movements of the plunger are required. Additionally, at such low infusion rates, friction between the plunger and the reservoir causes a jerking effect, known as stiction, and the fluid is delivered as a series of small boluses instead of a steady, continuous flow. The larger the cross-section of the plunger, the larger its circumference, which concomitantly increases stiction, requiring higher motor forces to overcome, and therefore increasing battery drain. A long, narrow medication reservoir having a small cross-section plunger encounters lesser stiction in translation, as well as other mechanical noises, and therefore requires lower plunger force for fluid displacement. A smaller cross section, and therefore a long aspect ratio, subsequently facilitates more accurate delivery of a low basal dosage at a lower power demand. A small cross-section plunger also experiences less force due to differential pressure between the inside and outside of the tube.

A long aspect ratio reservoir, however, poses a design challenge in compact infusion pumps. FIG. 1 demonstrates a conventional syringe-type pump 10. Pump 10 comprises a reservoir body 12 having a length x, a plunger 14 for receiving/expelling a fluid within reservoir body 12, a lead screw 16, and a plunger rod 18 for driving plunger 14 through the length x of the reservoir body 12. As illustrated in FIG. 1, a rigid, rectilinear plunger rod 18 would have to be at least as long as reservoir body 12 in order to displace plunger 14 along the entire length of the reservoir body; that is, the total length of the syringe-type pump 10 would be approximately 2× when reservoir body 12 is completely filled with medication. Consequently, a long, rectilinear plunger rod can potentially dominate the size of a small, compact infusion pump and make implementation of such a pump very difficult.

A second aspect of the present disclosure is a method and system for employing a long aspect ratio medication reservoir within an infusion pump of small footprint. In exemplary embodiments, a long syringe-type reservoir is implemented in the form of a long, curved reservoir. In one such embodiment, the long, curved reservoir comprises alternating curved and straight sections. In another embodiment, the reservoir has at least one straight section. In yet another embodiment, the reservoir is curved throughout its length. FIG. 2 illustrates a long, curved reservoir 20 for use in an infusion pump. Curved reservoir 20 comprises a tube 22 having a reservoir terminal 26. Tube 22 is connected to the reservoir terminal 26 using, for example, an O-ring, an adhesive sealant, etc. In exemplary embodiments, the dimensions of tube 22 are determined by the volume of medication intended for the reservoir. In some exemplary embodiments designed for the delivery of 2.20 cc of medication, the possible ratios of lengths (mm) and inner diameters (mm) of the reservoir tube 22 (having a circular cross-section) can be as follows: 28.0/10.0; 57.2/7.0; 129.5/4.7; or 311.2/3.0.

Tube 22 is constructed of a material that is compatible with the medication that the reservoir is intended to store and dispense. In illustrative embodiments, tube 22 is made of a metal, for example, stainless steel. In other embodiments, tube 22 is made of a polymeric material. In exemplary embodiments, tube 22 is made of high density polyethylene (HDPE). In some embodiments, flexible HDPE tubing is extruded as a single piece and then formed into the desired configuration by bending, and other techniques. An exemplary HDPE extruded tube 22 has a circular cross-section. The wall thickness of one such HDPE extruded tube 22 is about 1 mm or less. In another embodiment, square cross-section extrusion is used to form reservoir tube 22. In exemplary embodiments, the inner diameter of tube 22 is consistent throughout its length to maintain a hermetic seal between the plunger and the inner wall of the tube. Further, in certain embodiments, care is taken to minimize surface defects on the inner wall of tube 22, since surface defects can potentially result in excessive friction between the plunger and the inner wall of tube 22, as well as leakage of medication from the reservoir. In some embodiments, the inner surface of tube 22 is provided with a surface coating to lower friction with the plunger. Care is taken to choose a surface finish that is compatible with the medication. Certain low friction materials, such as PTFE (polytetrafluoroethylene) and FEP (fluorinated ethylene propylene) can also be used to form reservoir 20 and do not require low friction coating of their inner wall.

Another aspect of the present disclosure is a delivery mechanism for dispensing fluid from curved reservoir 20. In exemplary embodiments, fluid is dispensed by driving a plunger through curved reservoir 20 using a flexible plunger rod that can conform to a given shape of curved reservoir 20 and by accurately controling the forward displacement of the plunger or piston. In exemplary embodiments, the flexible plunger rod comprises a drive train 34 having an assembly of interconnected ball segments 36, as illustrated in FIG. 3A. Drive train 34 is configured to travel through any given geometry of curved reservoir 20. In some embodiments, drive train 34 is driven by a lead screw 38. In one such embodiment, lead screw 38 has a profile which allows lead screw rotation to transmit force to drive train 34, but does not allow drive train 34 to drive lead screw 38 in reverse when the drive train is subjected to a strong longitudinal force.

Drive train 34 comprises a plunger 32 attached at a proximal end (the end that is proximate a medication delivery port when curved reservoir 20 is empty) and a cursor 33 attached at a distal end (the end that is farthest away from the medication delivery port) of the assembly of ball segments. Throughout the rest of this disclosure, the end of the drive train (or the end of the reservoir) that is proximate to the medication delivery port is referred to as the proximal end.

Figure 3B:
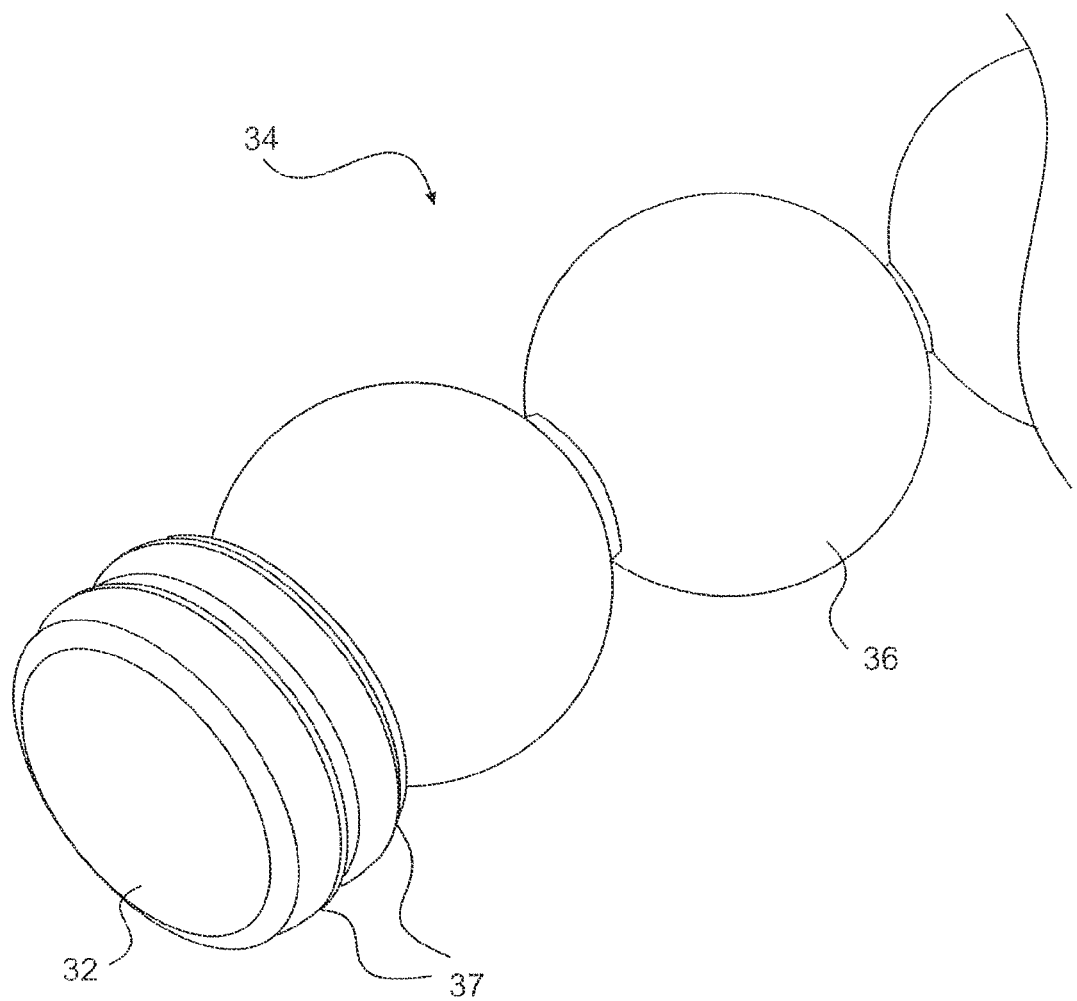
FIG. 3B illustrates a close-up view of a plunger at the proximal end of the drive train embodiment depicted in FIG. 3A.

In exemplary embodiments, cursor 33 functions as a sensor that can indicate the position of the drive train within the reservoir, and thereby denote the level of medication within the reservoir (described in detail later in this disclosure). FIG. 3B shows a close-up view of plunger 32 at the proximal end of drive train 34. In exemplary embodiments, as illustrated in FIG. 3B, plunger 32 comprises a supporting core with two elastomeric O-rings 37 extending radially outwards. The O-rings are configured to provide hermetic seal between plunger 32 and the inner wall of curved reservoir 20. In some embodiments, plunger 32 is configured to be compressible. In one such embodiment, plunger 32 is an elastomeric ball plunger configured to facilitate travel through the changing curvature of reservoir 20. In an alternative embodiment, plunger 32 is a ball plunger comprising a rigid sphere with an elastomeric outer shell. Additional plunger configurations can include x-rings, flanged elastomeric cap, etc., designed to achieve hermetic seal and low-friction movement between plunger 32 and inner wall of curved reservoir 20.

FIGS. 4A-4C illustrate a method of filling curved reservoir 20 with medication. For ease of illustration, curved reservoir 20 is depicted as a straight reservoir in FIGS. 4A-4C. As would be understood by a person of ordinary skill in the art, the following method of filling a syringe-type reservoir can be used with both a curved and a straight reservoir. During the fill stage, drive train 34 is not connected to lead screw 38. Reservoir 20 is delivered to a user with plunger 32 bottomed out at a proximal end 42 of reservoir 20, as shown in FIG. 4A. As the user fills the reservoir with medication using a fill syringe, plunger 32 and drive train 34 are driven back towards a distal end 44 of reservoir 20, as shown in FIG. 4B. In one exemplary embodiment, reservoir 20 is filled with medication via a fill port that is separate and distinct from a medication dispensing port through which medication is supplied to a user. In another exemplary embodiment, the fill port and the medication dispensing port are the same. Further details about the fill port and the medication dispensing port are provided later in this application in reference to an exemplary infusion pump.

Referring again to FIG. 4B, drive train 34 is located either within the reservoir 20, or in a feeder track 31, depending on the position of plunger 32 within reservoir 20. When reservoir 20 is completely filled with the medication, drive train 34 is located completely within feeder track 31. Lead screw 38 then engages drive train 34 at a proximal section of feeder track 31, as depicted in FIG. 4C. As a result of the lead screw rotation, drive train 34 travels in the forward direction towards proximal end 42 of the reservoir to supply medication to the user. In some exemplary embodiments, the delivery mechanism is specifically designed to prevent back-driving, i.e., to prevent drive train 34 from traveling in the reverse direction towards the distal end of reservoir 20. This mechanism prevents curved reservoir 20 from being refilled with medication more than once, and thus, requires reservoir module 120 to be disposed of after a single use.

Figure 5:
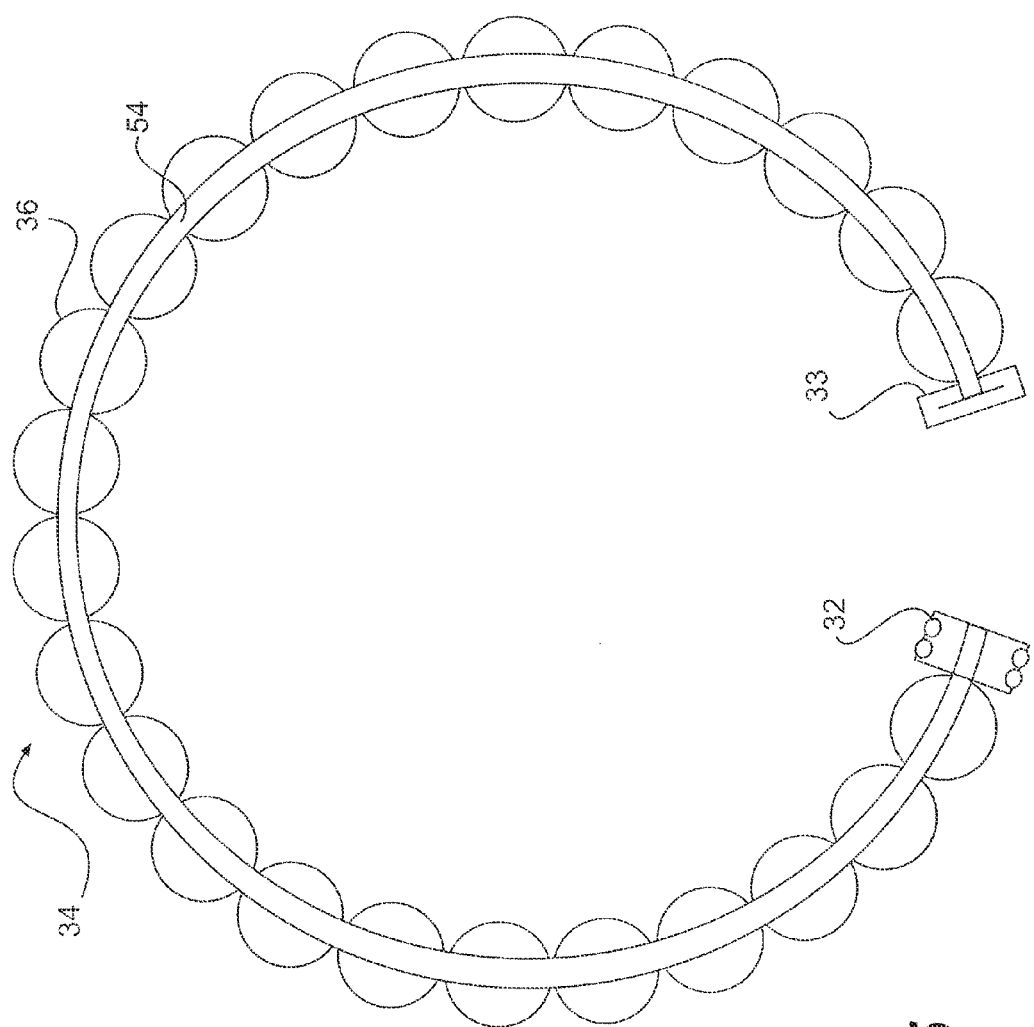
FIG. 5 illustrates a cross-sectional top view of the drive train embodiment depicted in FIG. 3A.

In exemplary embodiments, the assembly of ball segments 36 is configured to be incompressible and flexible. FIG. 5 is a cross-sectional view of an exemplary embodiment of drive train 34. As illustrated in FIG. 5, drive train 34 comprises a series of ball segments 36 each having a through hole to receive a filament 54 that connects all the components together starting at plunger 32 at the proximal end and cursor 33 at the distal end. In one such embodiment, ball segments 36 comprise 4.5 mm round rigid balls each having a 1 mm through hole. The rigidity of ball segments 36 ensure that drive train 34 is not compressed or deformed during operation. In exemplary embodiments, filament 54 is flexible and elastic, which allows bending of drive train 34 to facilitate travel through the curvature of reservoir 20 and feeder track 31. In certain embodiments, the length of filament 54 is selected to maintain drive train 34 under slight axial compression. The flexibility and elasticity of filament 54, along with the slight compressive force keeping all the ball segments 36 in direct contact, ensure that successive ball segments 36 are pulled up to lead screw 38 without a gap between them.

Figure 6B:
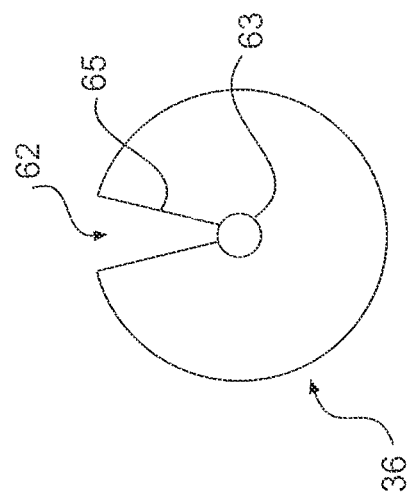
FIG. 6B illustrates a close-up view of a ball segment of the drive train embodiment depicted in FIG. 6A.
Figure 6A:
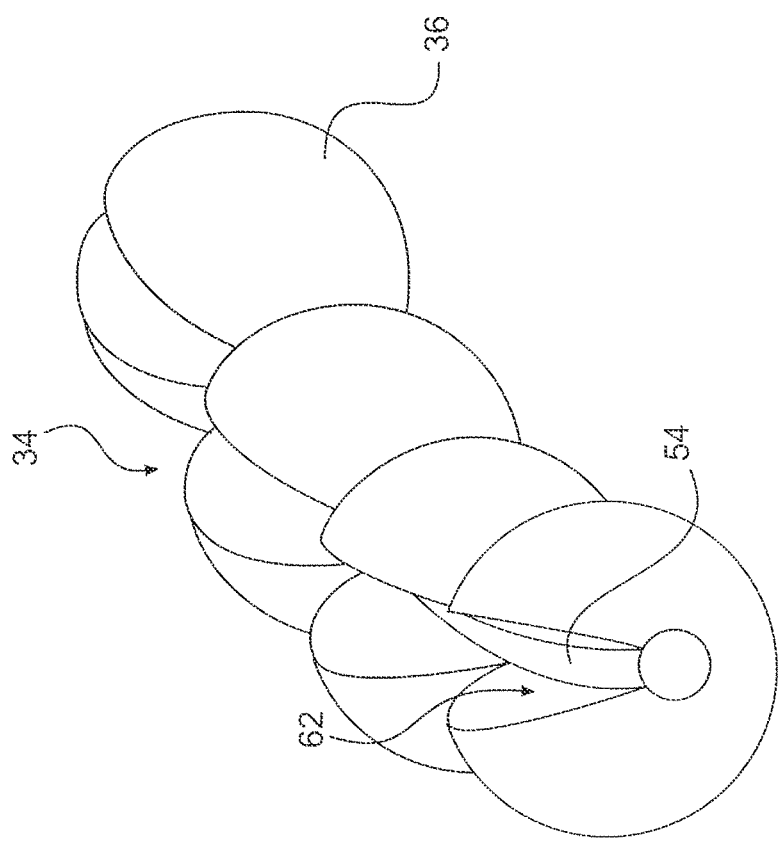
FIG. 6A illustrates an alternative drive train having an assembly of interconnected ball segments, in accordance with exemplary embodiments of the present disclosure.

FIG. 6A illustrates an alternative embodiment of drive train 34 designed to facilitate the assembly process. In one such embodiment, ball segments 36 comprise a keyhole feature 62 having a center hole 63 and a tapered slot 65. FIG. 6B is a close-up view of a ball segment 36 comprising keyhole 62. Keyhole 62 is configured such that the diameter of center hole 63 is smaller than the width of slot 65 at the outermost portion of the keyhole, but bigger than the width of the slot at its innermost portion. To assemble drive train 34, ball segments 36 are positioned with their slots aligned. Filament 54, which has a diameter bigger that the smallest width of the tapered slot 65, is stretched to decrease its diameter. This allows filament 54 to be lowered into center holes 63 of the ball segments all at once. Once the stretched filament is lowered into center holes 63, the filament is released and allowed to regain its original diameter. Since the original diameter of filament 54 is larger than the smallest width of tapered slot 65, the filament cannot pass through the slot and is permanently captured within center holes 63 of the ball segments 36.

In another alternative embodiment, the components of drive train 34, that is, ball segments 36, plunger 32, and cursor 33, are interconnected using a tongue and groove system 72. FIG. 7A illustrates drive train 34 having a tongue and groove system 72, and FIG. 7B shows a cross-sectional view of a ball segment 36 having a tongue 74 and a groove 76. In one such embodiment, filament 54 is not required; the components of the drive train are interconnected by inserting the tongue of one ball segment 36 into the groove of the successive ball segment. In exemplary embodiments, tongue and groove system 72 is incorporated into plunger 32 and cursor 33 to connect them to adjoining ball segments.

Figure 8A:
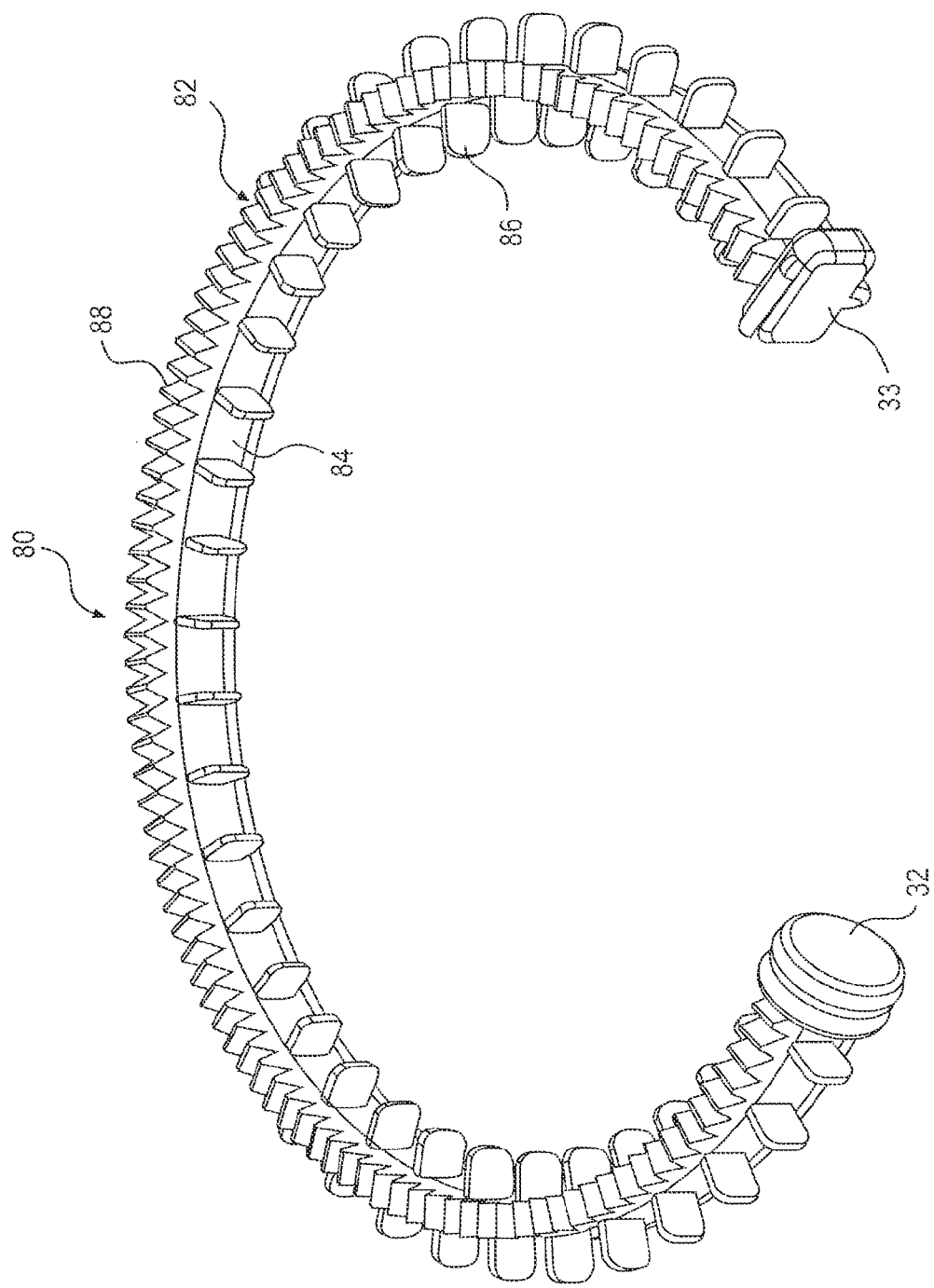
FIG. 8A illustrates a single-piece drive train, in accordance with exemplary embodiments of the present disclosure.
Figure 8B:
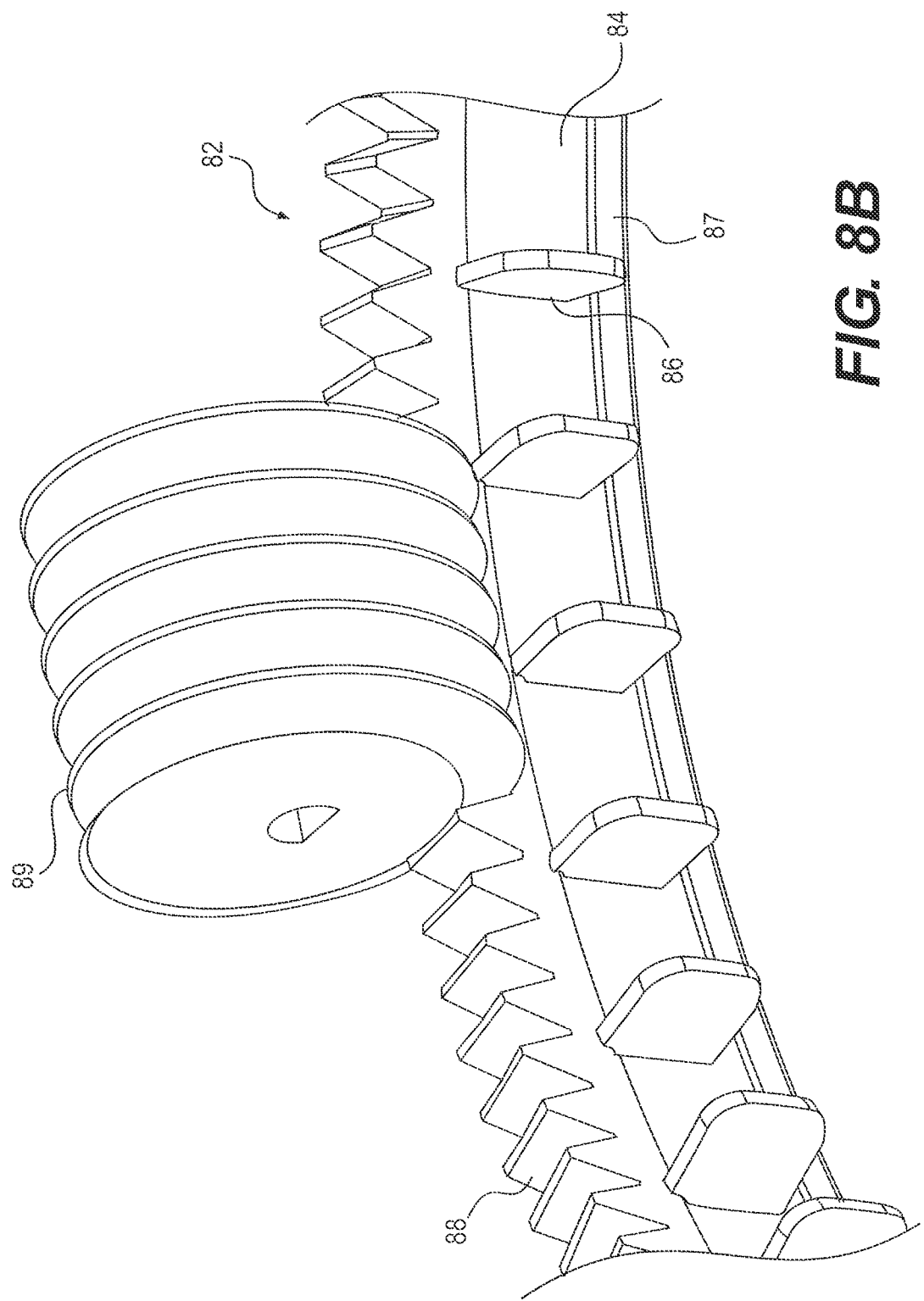
FIG. 8B illustrates a close-up view of the single-piece drive train embodiment depicted in FIG. 8A along with the lead screw component driving the drive train.

In yet another alternative embodiment, the drive train comprises a single component instead of multiple components assembled together. Such an embodiment is referred to hereinafter as a single-piece drive train 80. In certain embodiments, drive train 80 is injection molded using a polymeric material that resists axial compression while providing sufficient flexibility to the drive train to steer through curved reservoir 20. Drive train 80 comprises a threaded spine 82, and plunger 32 and cursor 33 connected to the proximal and distal ends, respectively, of threaded spine 82. Threaded spine 82 comprises a center structure 84 with a continuous thread 88 on top of the structure. In some embodiments, drive train 80 further comprises centering elements 86 on each side of center structure 84, as shown in FIG. 8A. In another embodiment, centering elements 86 are present on only one side of center structure 84. The number of centering elements required and their location is entirely dependent on the inner profile of curved reservoir 20 and the mechanical properties of drive train 80. Centering elements 86 help to position threaded spine 82 within the curved reservoir 20. FIG. 8B shows a close-up view of an exemplary drive train 80 in engagement with a lead screw 89 specifically intended for threaded spine 82. As shown in the figure, drive train 80 further comprises an alignment rail 87 located at the bottom of threaded spine 82. Alignment rail 87 is used to ensure that drive train 80 is properly positioned as it passes under lead screw 89 and that threads 88 align with the grooves of the lead screw.

Figure 9A:
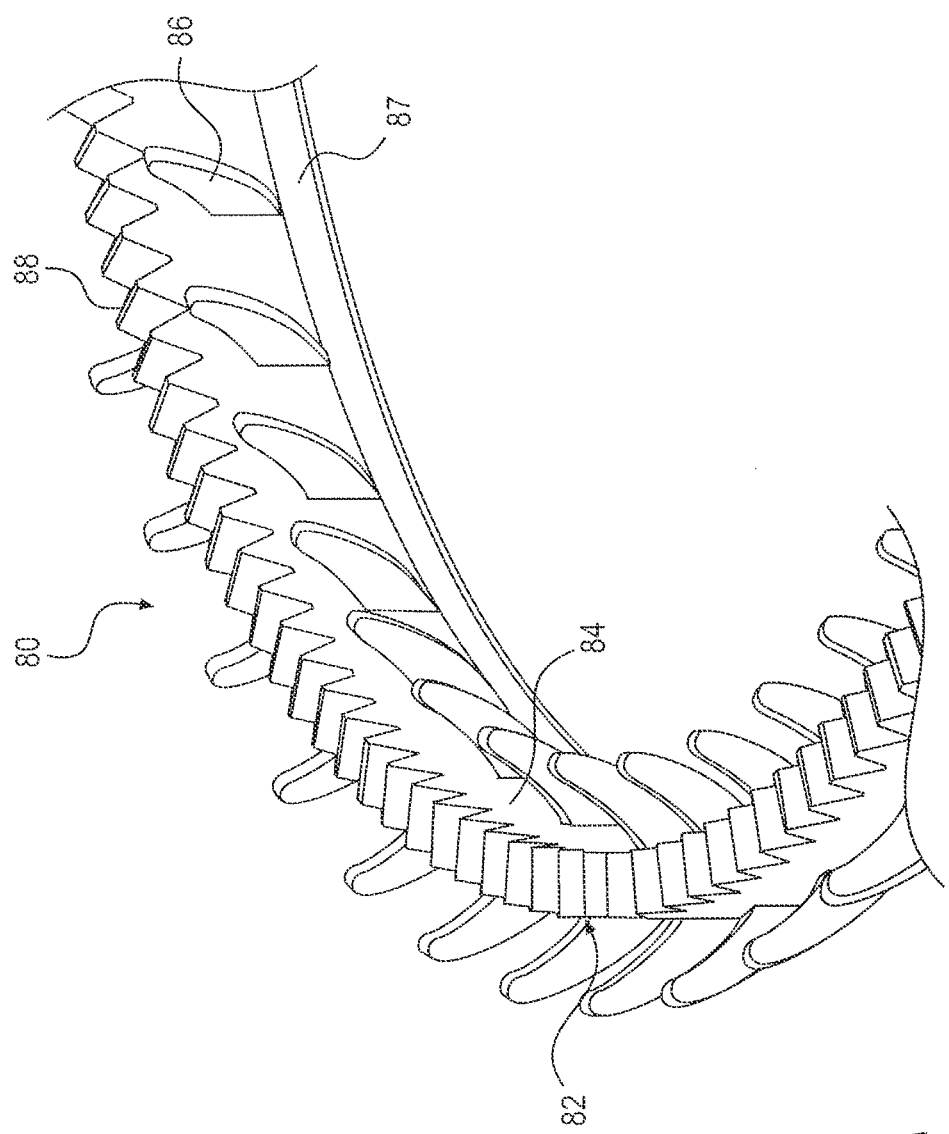
FIG. 9A illustrates a different configuration of centering elements for the single-piece drive train embodiment depicted in FIG. 8A.
Figure 9B:
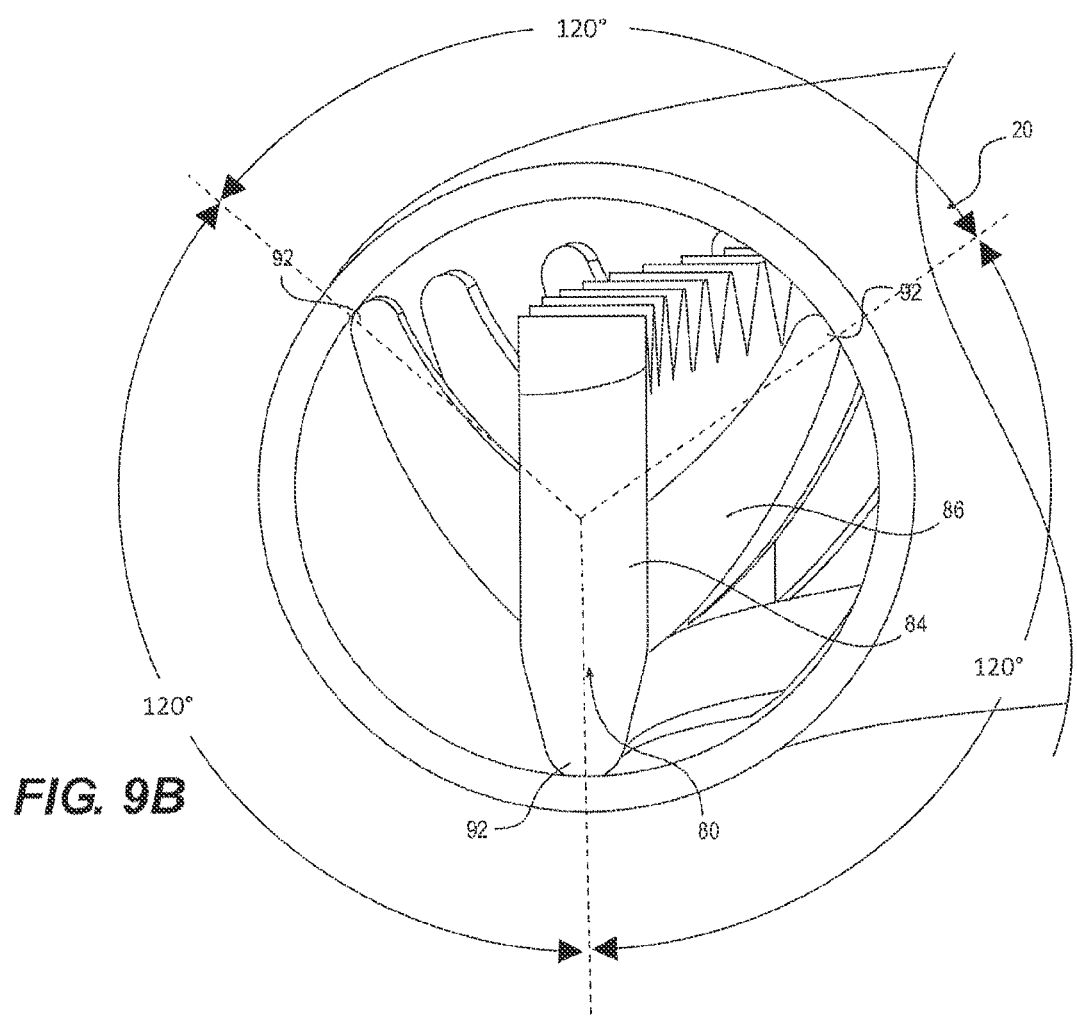
FIG. 9B illustrates the single-piece drive train embodiment depicted in FIG. 9A as positioned within an exemplary curved reservoir.

FIG. 9A shows an alternative embodiment of centering elements 86 of single-piece drive train 80. This particular design makes centering elements 86 more flexible in lateral displacement, and therefore, more tolerant to slight variations in the shape or dimension of curved reservoir 20. FIG. 9B shows a cross-section of drive train 80 positioned within curved reservoir 20. To minimize friction with the inner surface of reservoir 20, and to optimize the centering of drive train 80, the number of contact points 92 is limited to three (3) for any given cross-section, and the contact points are located approximately 120° apart.

Another aspect of the present disclosure is an infusion pump encompassing a long, curved reservoir and a delivery mechanism comprising a flexible drive train for controlled, accurate delivery of small amounts of fluidic medication from the reservoir. The configuration of an exemplary infusion pump will be described with reference to curved reservoir 20, drive train 80, and lead screw 89. It is contemplated that the infusion pump of the present disclosure can utilize a long, curved reservoir and a flexible drive train of any configuration, including, but not limited to drive train 34 and lead screw 38.

Figure 10A:
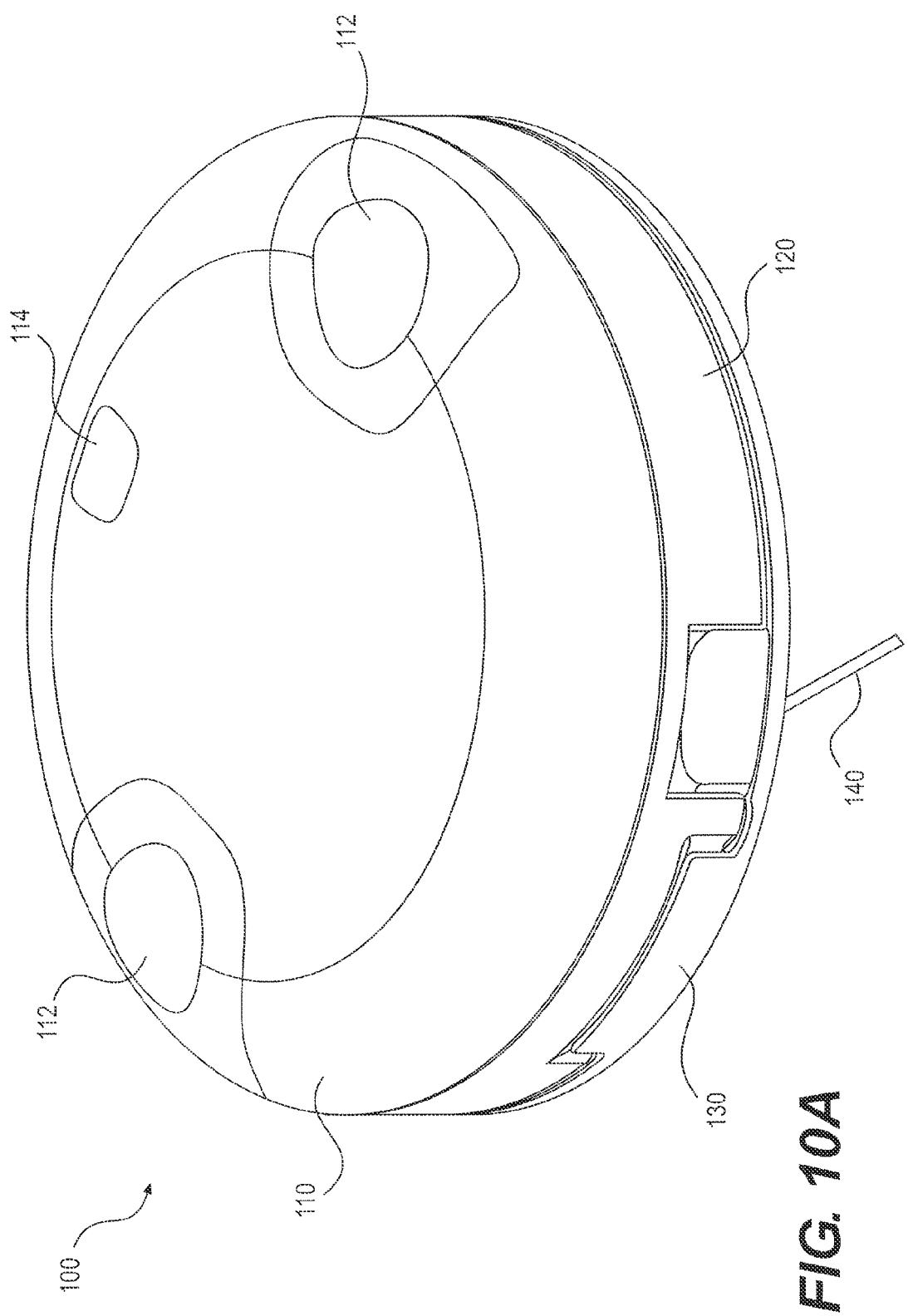
FIG. 10A illustrates a modular infusion pump, in accordance with exemplary embodiments of the present disclosure.
Figure 10B:
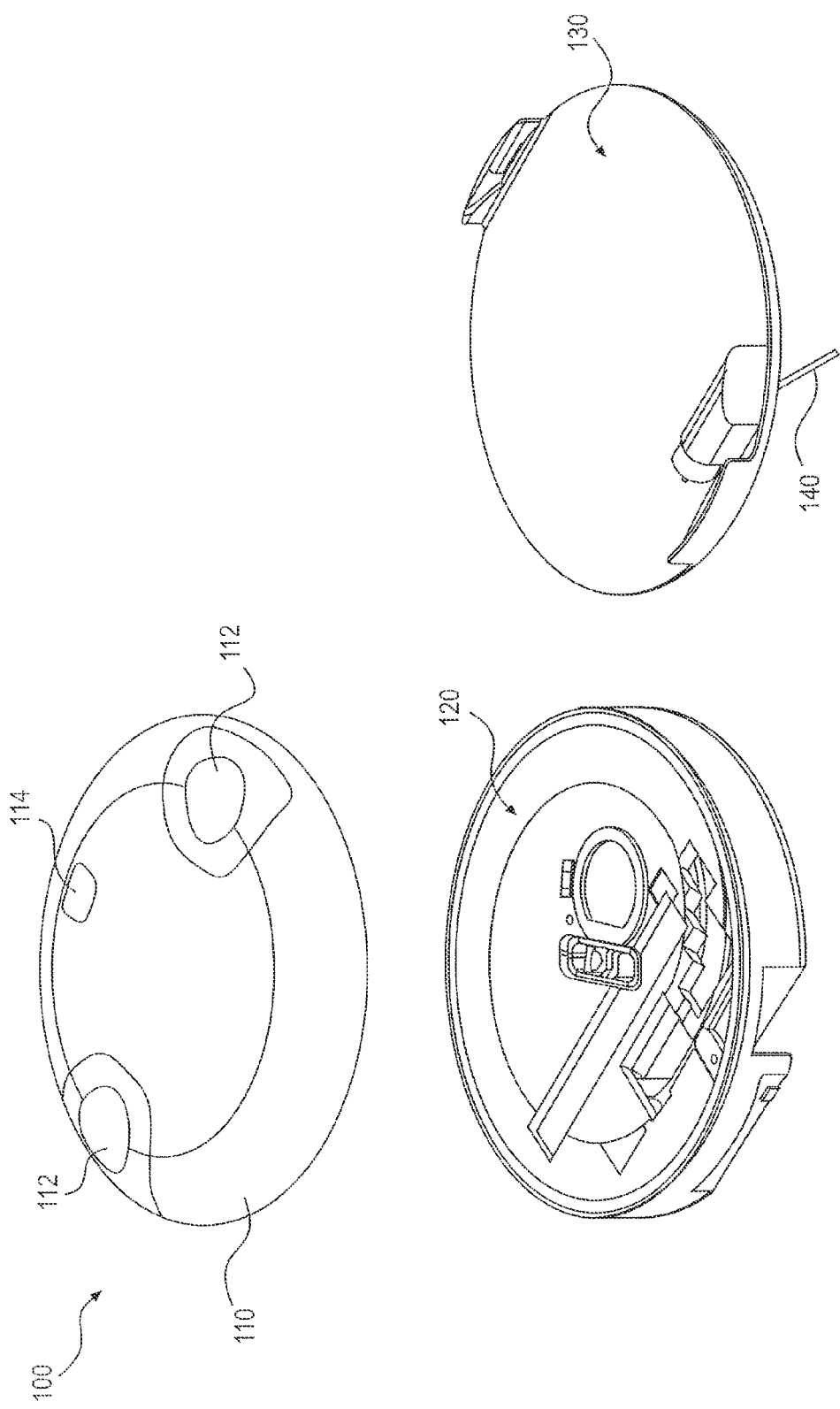
FIG. 10B illustrates an exploded view of the infusion pump embodiment depicted in FIG. 10A.

FIG. 10A demonstrates a general configuration of a modular infusion pump 100 comprising a control module 110, a reservoir module 120, and a cradle 130. FIG. 10B is an exploded view of the embodiment depicted in FIG. 10A and shows control module 110, reservoir module 120 and cradle 130 separated from one another. In exemplary embodiments, control module 110 and reservoir module 120 are mated and locked together to form a pump unit, which is then connected to cradle 130. Cradle 130 is configured to adhere directly to the skin of a user. A flexible cannula 140 extends below the bottom surface of the cradle and penetrates the skin of the user to deliver the medication. In exemplary embodiments, control module 110 comprises the electronics and the motor of infusion pump 100, including lead screw 89, and reservoir module 120 includes curved reservoir 20, drive train 80, and a battery to power the infusion pump. In some embodiments, lead screw 89 is included in the reservoir module 120 instead of control module 110. Reservoir module 120 is manually filled with medication by the user before attaching it to control module 110. In one embodiment, infusion pump 100 is a semi-disposable device, wherein reservoir module 120 and cradle 130 are disposable while the control module 110 can be re-used multiple times with new reservoir modules 120 and cradles 130. In such an embodiment, the fluidic pathway is contained entirely within the disposable reservoir module 120, and therefore, multiple uses of control module 110 do not pose any risk of cross-contamination or degradation of residual medication within the reservoir. In another embodiment, all of the components of infusion pump 100, including control module 110, are fully disposable.

In exemplary embodiments, as illustrated in FIGS. 10A and 10B, control module 110 can further comprise at least one bolus button 112 to signal the pump to provide a bolus of medication to the user, and a visual indicator 114 to notify the user of certain events or status. In select embodiments, control module 110 is configured to communicate with an implantable and/or a skin-attached disease-monitoring device to form a closed-loop system that allows manual or automatic adjustment of dosage based on the readings from the disease-monitoring device. For instance, if modular infusion pump 100 is intended for continuous delivery of insulin, then control module 100 can be configured to receive feedback from a Continuous Glucose Monitor (CGM) and to adjust the insulin dosage accordingly.

Figure 11:
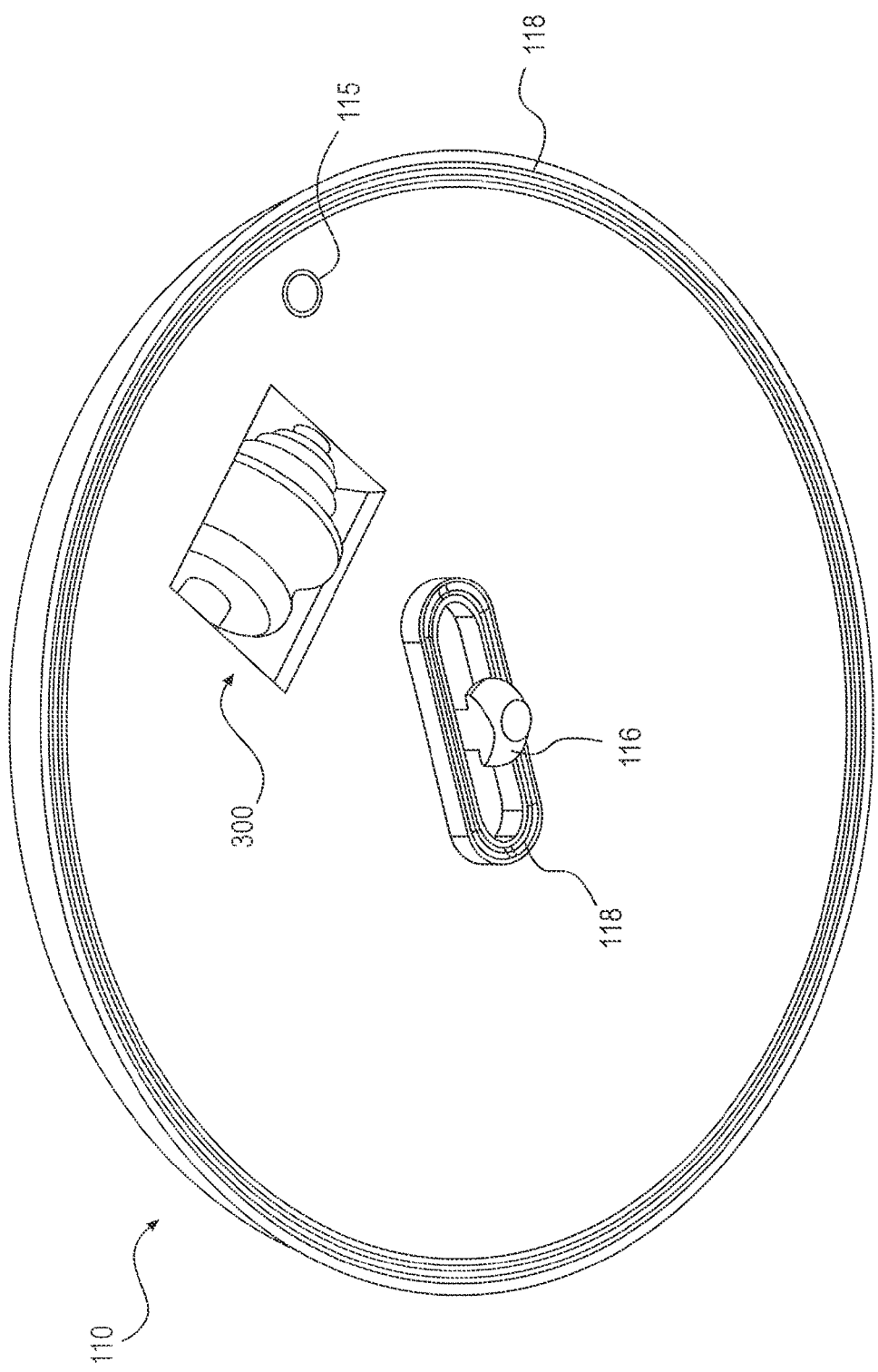
FIG. 11 illustrates the underside of the control module of the infusion pump embodiment depicted in FIGS. 10A and 10B.

FIG. 11 illustrates the underside of control module 110 in an exemplary embodiment of infusion pump 100. In one embodiment, control module 110 comprises a locking pin 116 projecting beyond the bottom surface of the control module. Locking pin 116 penetrates reservoir module 120 to secure the control module to the reservoir module. FIG. 11 also illustrates an output mechanism 300 positioned within control module 110. Output mechanism 300 delivers mechanical actuation to drive train 80 to dispense fluid from curved reservoir 20. In exemplary embodiments, control module 110 comprises an electric motor and a gearbox (described in detail later in this disclosure). An output shaft of the electric motor is coupled to the gearbox, which increases the torque provided by the electric motor and increases the rotational resolution. The output of the gearbox is mechanically coupled to output mechanism 300, which comprises a drive shaft and lead screw 89. The drive shaft receives rotational motion from the gearbox and transmits it to lead screw 89 which rotates along with the drive shaft. Lead screw 89 also has the ability to slide laterally along a flat surface on the drive shaft, which allows the lead screw to self-align when engaging the threaded spine of drive train 80, as described later in this disclosure.

In exemplary embodiments, control module 110 can comprise one or more annular seals 118 on the bottom surface of control module 110 to form a hermetic seal between control module 110 and reservoir module 120. As illustrated in FIG. 11, a first annular seal 118 can be located around the periphery of the bottom surface of control module 110 and a second annular seal 118 is located around locking pin 116. In one embodiment, annular seals 118 comprise elastomeric gaskets (for example, O-rings or overmolded features) that form a sealing contact between control module 110 and reservoir module 120. In certain embodiments, control module 110 can further comprise a sensor 115, such as a mechanical, optical or magnetic sensor, to determine whether the pump unit (control module and reservoir module) is installed on cradle 130 or not.

Figure 12:
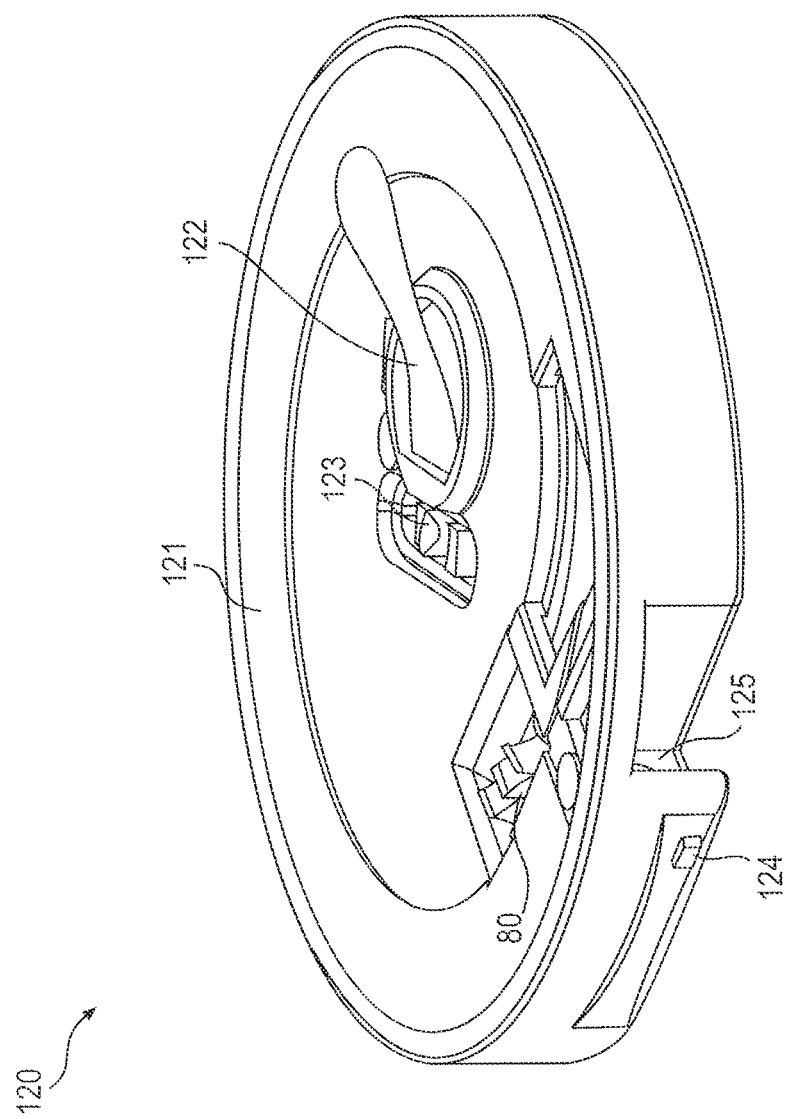
FIG. 12 illustrates a top-view of the reservoir module of the infusion pump embodiment depicted in FIGS. 10A and 10B.

FIG. 12 shows a top view of an exemplary reservoir module 120 having a lid 121 attached to its top surface. Several openings in lid 121 provide access to components positioned within the reservoir module, such as a battery 122 (shown with activation tab), and latching tabs 123 used to latch onto locking pin 116 of control module 110 when the control module is properly aligned on the reservoir module. The locking mechanism (i.e., engagement of locking pin 116 by latching tabs 123 of the reservoir module) helps to orient and center the modules prior to mating and to prevent accidental disconnection of the modules after full engagement of the lock.

Referring again to FIG. 12, another opening in lid 121 exposes a few threads of drive train 80 that are engaged by lead screw 89 when control module 110 and reservoir module 120 are mated together. In exemplary embodiments, the housing of reservoir module 120 is equipped with a few raised (or recessed) structures 124 that can be used to secure the reservoir module to cradle 130. In exemplary embodiments, reservoir module 120 further comprises a port 125, which can be used to fill curved reservoir 20 with medication and also to connect reservoir module 120 to cradle 130 for delivery of medication to the user.

Figure 13B:
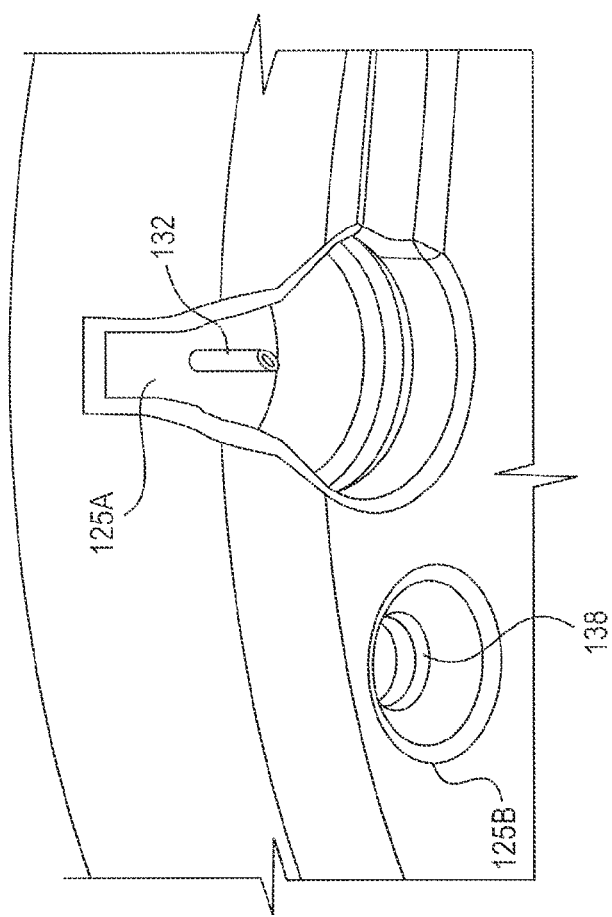
Figure 13A:
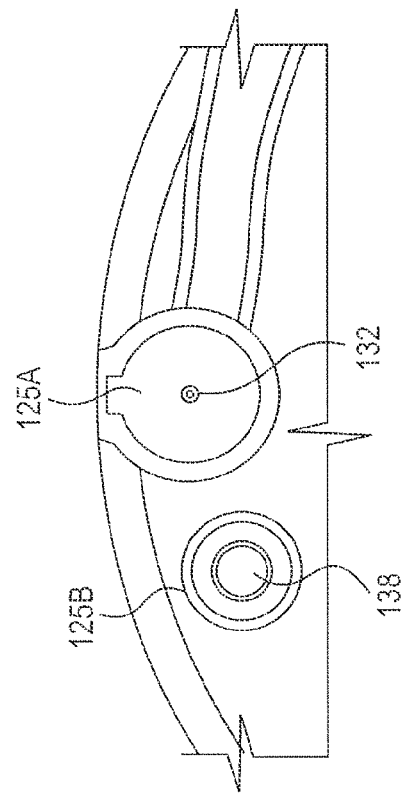
Figure 13D:
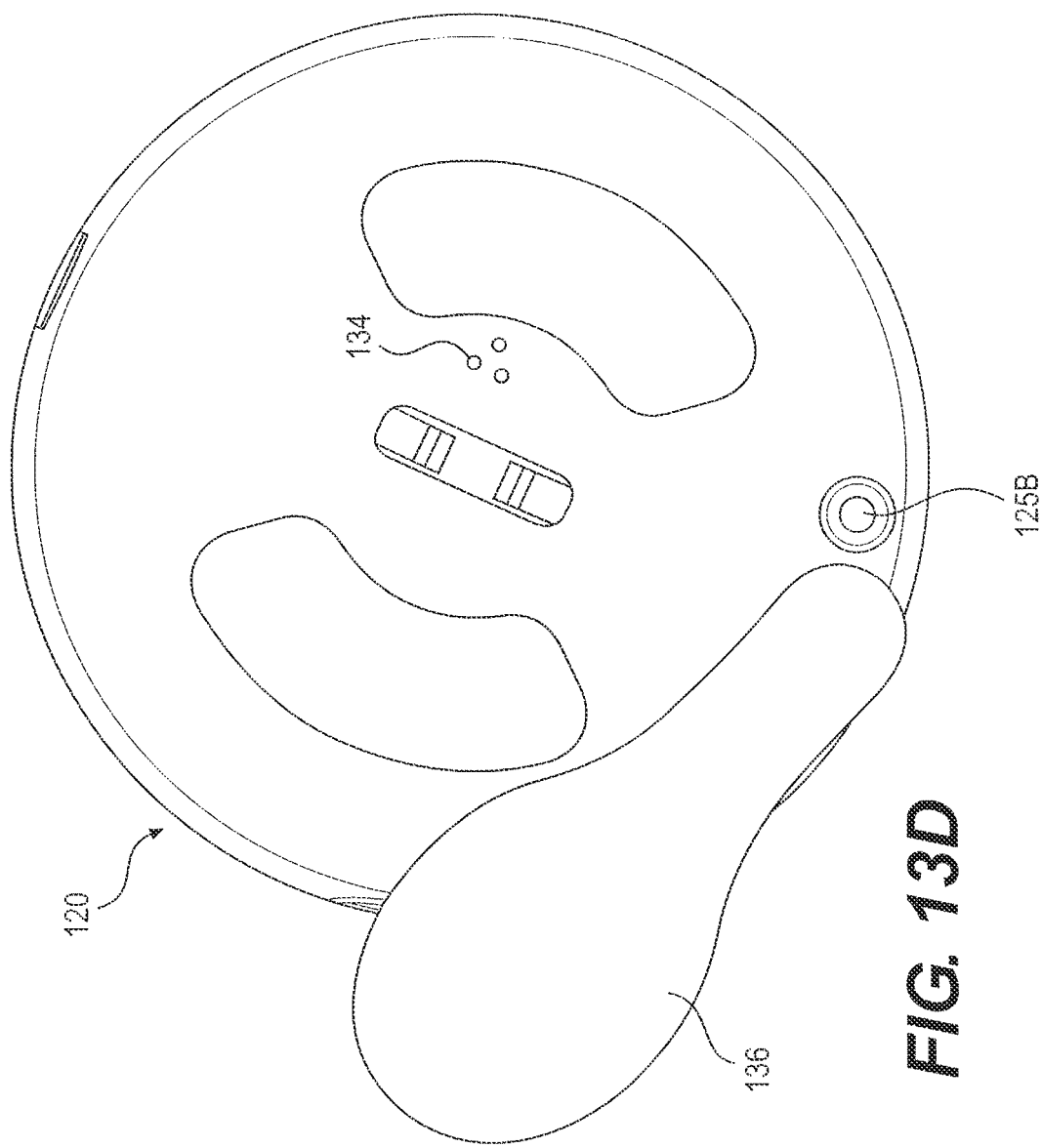
Figure 13E:
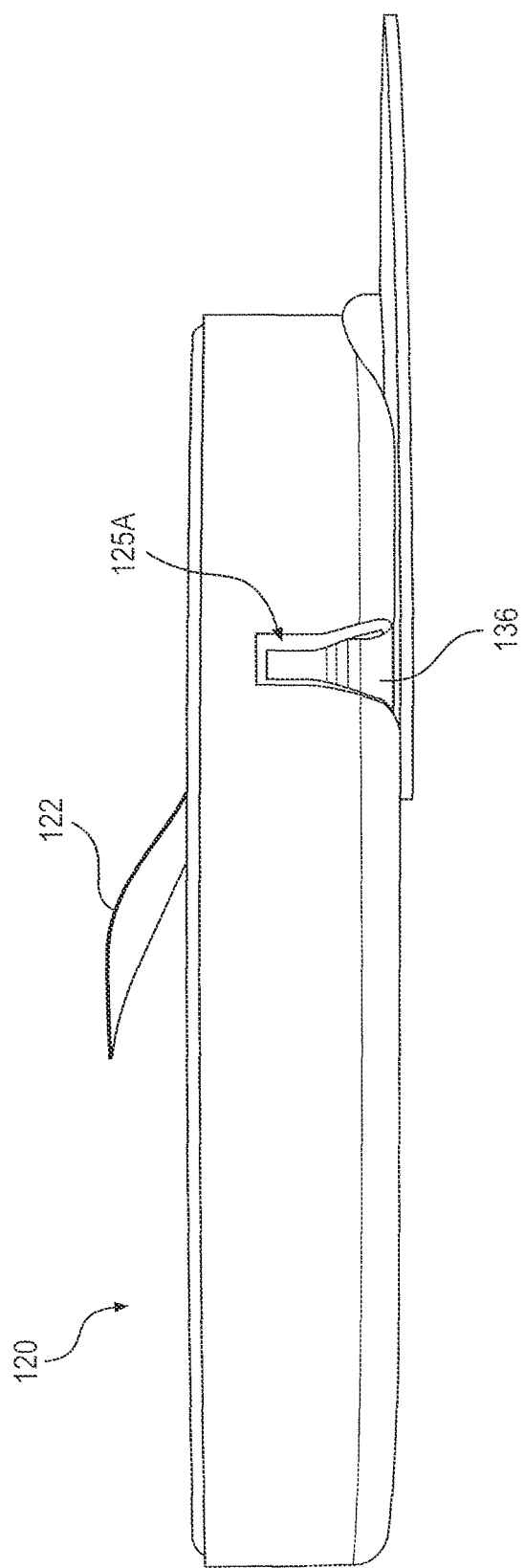

In some exemplary embodiments, the port used for dispensing medication is separate and distinct from a fill port used for loading medication into curved reservoir 20. FIGS. 13A, 13B, and 13C illustrate such an embodiment having two separate ports in reservoir module 120—an output port 125A used to deliver medication to a user and a fill port 125B used for loading medication into reservoir 20. In select embodiments, fill port 125B is a self-sealing port designed to avoid leakage of medication through the fill port during operation. FIG. 13A shows a bottom view and FIG. 13B shows a bottom isometric view of an exemplary reservoir module 120 having output port 125A and fill port 125B. In exemplary embodiments, output port 125A comprises a terminal junction needle 132 that can connect with a cradle 130 for delivery of medication to the user. In select embodiments, fill port 125B comprises a fill septum 138 that can be used to infuse medication into curved reservoir 20. The needle of a fill syringe containing the necessary volume of medication is inserted into fill septum 138 to inject the medication into the curved reservoir. In some embodiments, output port 125A is configured to attach to an infusion set 150 in place of cradle 130, as illustrated in FIG. 13C. Infusion set 150 comprises a tubing 152 with a cannula/insertion needle (not shown) at its proximal end for subcutaneous delivery of medication to a user. In certain embodiments, port 125 or output port 125A is capped with a protective plug 136 until it is connected to cradle 130 or infusion set 150. FIGS. 13D and 13E show a bottom view and side view, respectively, of an exemplary reservoir module having protective plug 136 over output port 125A. In select embodiments having a single port 125, protective plug 136 can function as a fill septum for loading medication into curved reservoir 20. In those embodiments that have discrete output port 125A and fill port 125B, protective plug 136 is used to prevent medication from escaping through output port 125A when medication is introduced into reservoir 20 through fill port 125B.

Once the reservoir is filled with the required volume of medication, reservoir module 120 is mated with control module 110 to form a pump unit. Protective plug 136 is then removed from the base of reservoir module 120. Cradle 130 or infusion set 150, which is already attached to the skin of the user, is then connected to port 125 or output port 125A to begin delivery of medication.

In exemplary embodiments, as illustrated in FIGS. 13C and 13D, the base of reservoir module 120 further comprises a hydrophobic vent 134. Vent 134 is provided to equalize the pressure inside and outside the reservoir module. In some embodiments, vent 134 is composed of a hydrophobic membrane hermetically affixed to the interior surface of the reservoir module. In one such embodiment, the vent membrane is ultrasonically welded to the base of the reservoir module directly over the holes of vent 134. In an alternative embodiment, the membrane can be replaced by a plug of hydrophobic porous (breathable) material held within a receptacle.

Figure 14A:
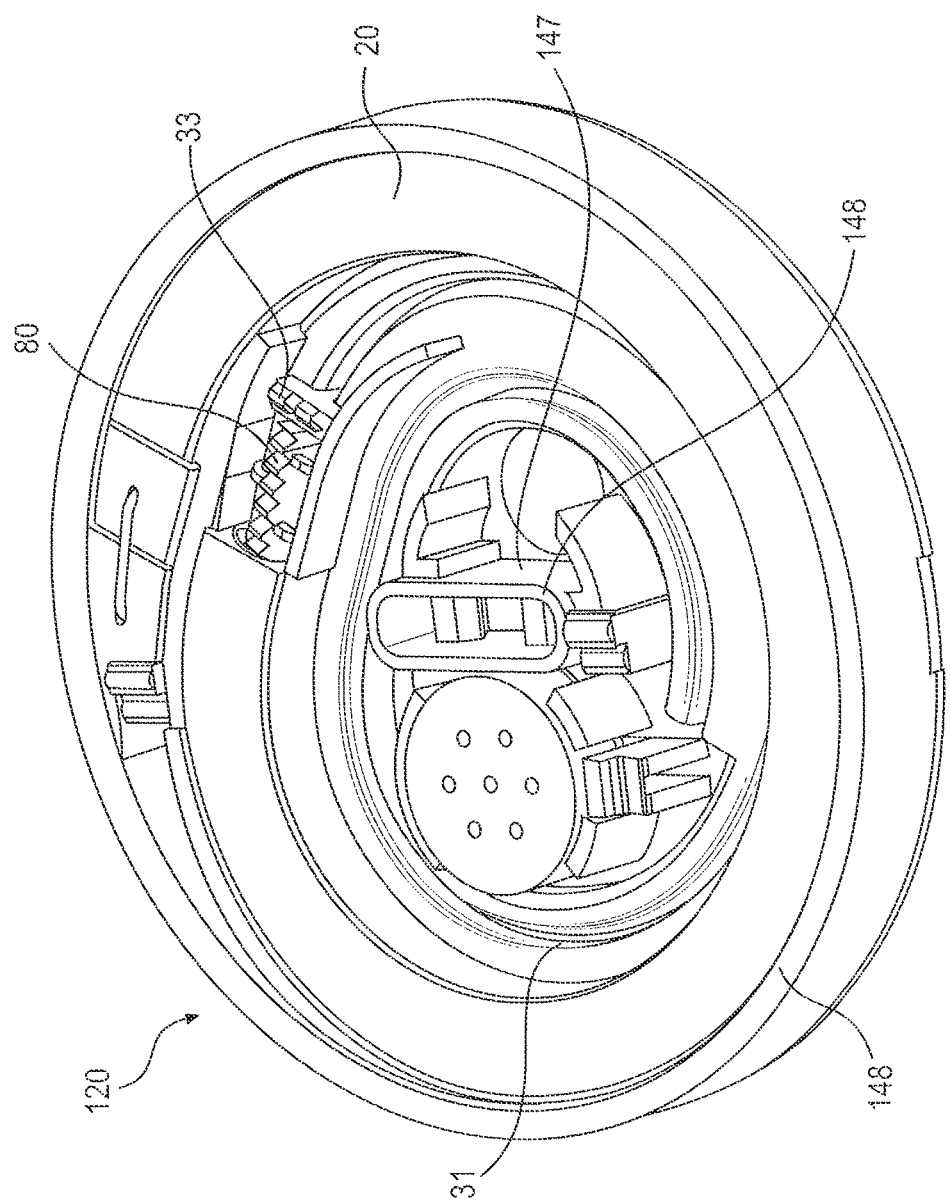
FIGS. 14A and 14B illustrate the interior components of the reservoir module of the infusion pump embodiment depicted in FIGS. 10A and 10B.
Figure 14B:
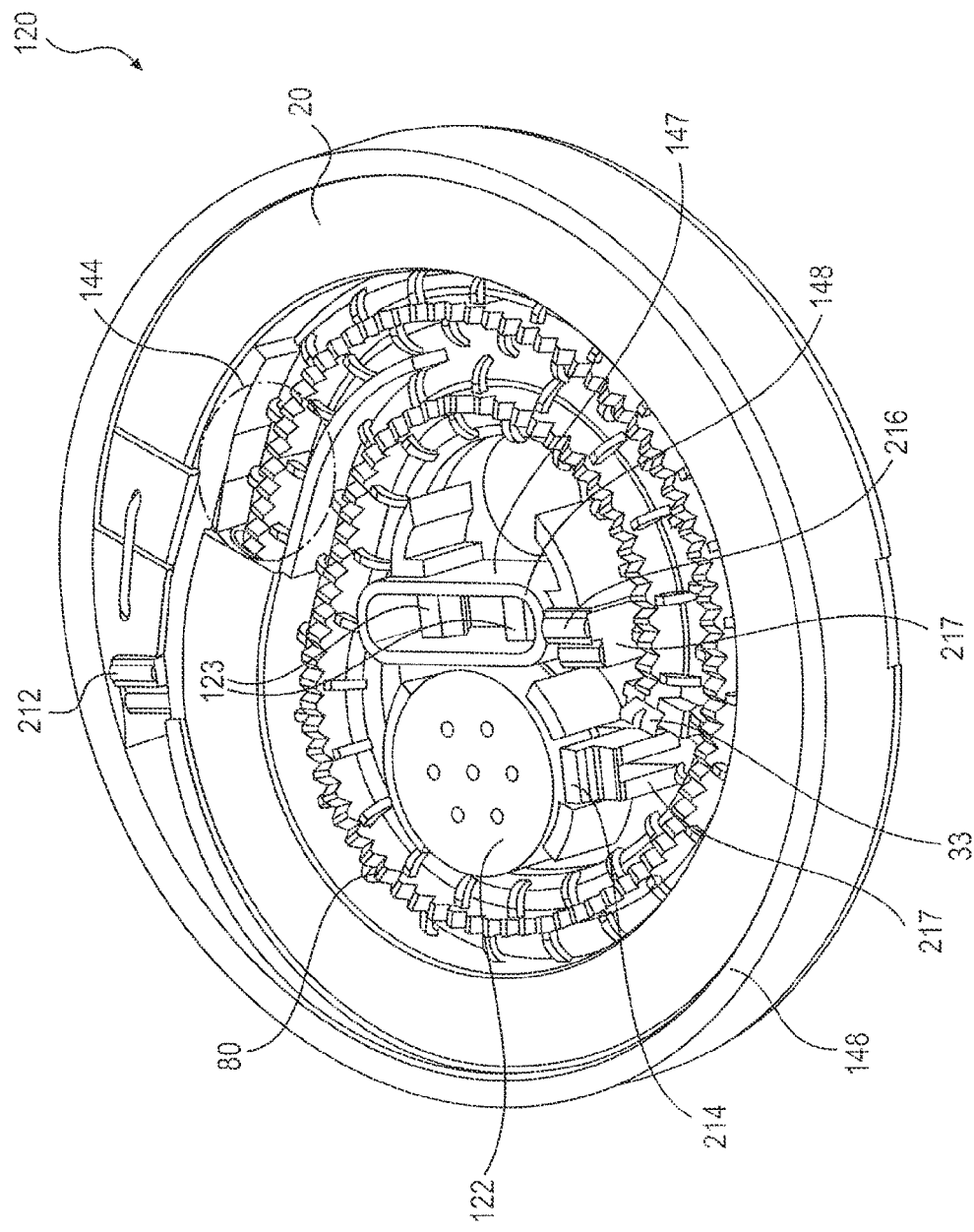

FIGS. 14A and 14B show the interior components of an exemplary reservoir module 120 comprising curved reservoir 20, drive train 80, and having a single port 125 used for both loading medication into reservoir 20 and to dispense medication to the user. Lid 121 of the reservoir module is removed to show the interior components of the reservoir module. FIG. 14A illustrates the interior of reservoir module 120 before curved reservoir 20 is filled with medication. Infusion pump 100 is delivered to a user with plunger 32 bottomed out at the proximal end (the end of the reservoir that is proximate to the port that delivers medication to the user) of curved reservoir 20, as shown in FIG. 14A. In this configuration, drive train 80 is contained almost entirely within the curved reservoir. As the user fills curved reservoir 20 with medication via port 125, plunger 32 and drive train 80 are driven back towards the distal end of curved reservoir 20, as shown in FIG. 14B. Depending on the position of plunger 32 within curved reservoir 20, drive train 80 is located either within the reservoir 20, or in feeder track 31. In exemplary embodiments, feeder track 31 comprises a continuous, curved wall structure that serves as a low friction track for guiding drive train 80. When reservoir 20 is completely filled with the medication, drive train 80 is located almost entirely on the feeder track 31, as depicted in FIG. 14B.

FIGS. 14A and 14B further illustrate battery 122, terminal junction needle 132, and a window 147 positioned within an illustrative embodiment of reservoir module 120. In some embodiments, battery 122 is placed on elastic support structures to elevate it and bring it in contact with control module 110. Junction needle 132 couples reservoir terminal 26 of the curved reservoir to port 125/output port 125A for delivery of medication to the user. Window 147 is provided to allow ingress of locking pin 116, which is used to secure reservoir module 120 and control module 110. Further, in some exemplary embodiments, overmolded gaskets 148 are provided around the periphery of window 147 and around the margin of reservoir module 120 to provide a hermetic seal between control module 110 and reservoir module 120. The locking mechanism of infusion pump 100 (engagement of locking pin 116 of the control module by latching tabs 123 of the reservoir module) helps to provide uniform compression around gaskets 148 and improve hermeticity of the pump.

Consistent with exemplary embodiments of the present disclosure, area 144 in FIG. 14B identifies the segment of drive train 80 that is engaged by lead screw 89 when reservoir module 120 is mated with control module 110. In exemplary embodiments, area 144 is a straight segment, which facilitates mechanical coupling between the drive train and the lead screw. In one such embodiment, drive train 80 is permitted to advance only in the proximal direction, i.e., towards output port 125A or port 125, once drive train 80 is engaged by lead screw 89.

Figure 15A:
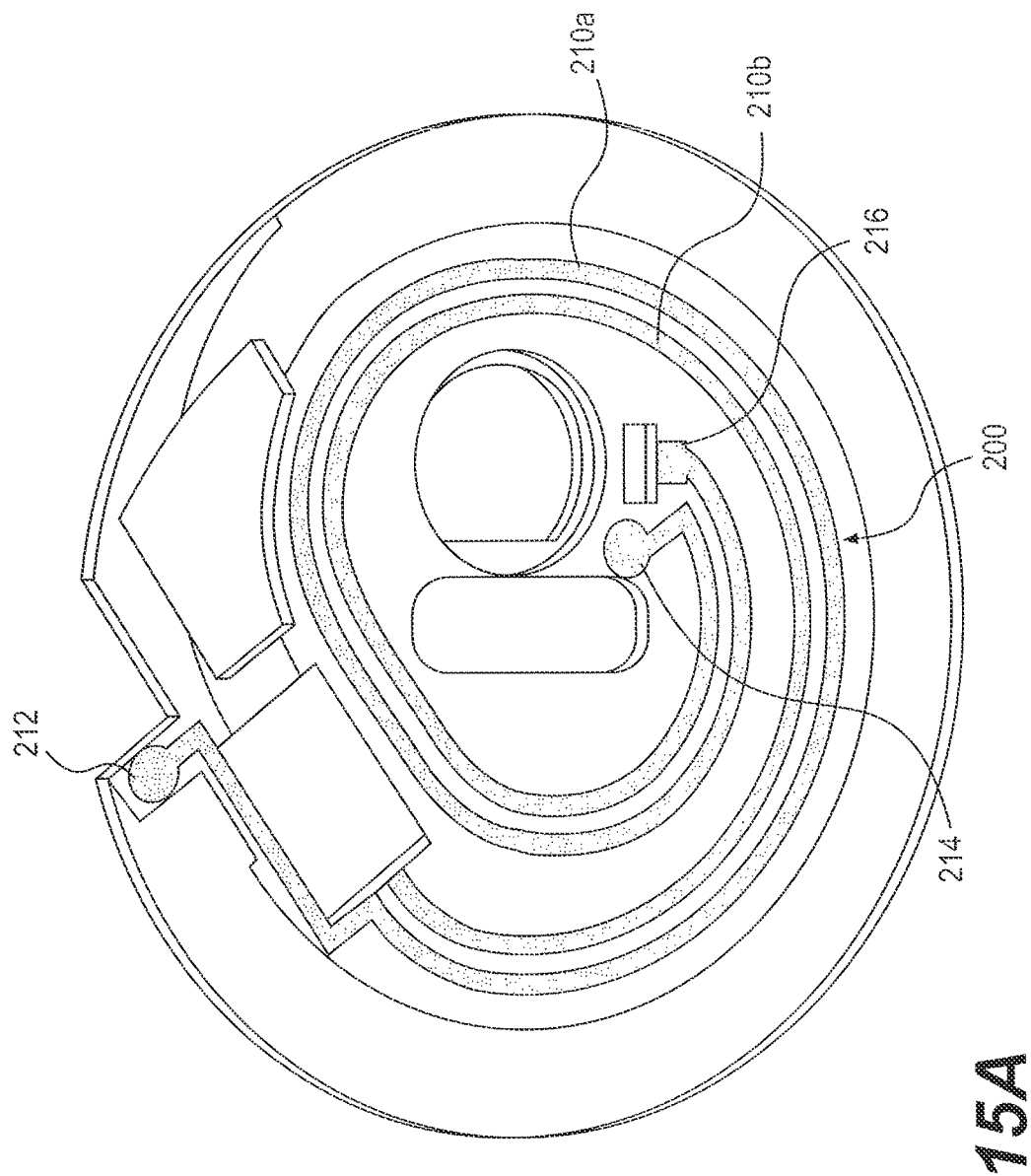
FIG. 15A illustrates a medication level sensing system, in accordance with exemplary embodiments of the present disclosure.

A yet another aspect of the present disclosure is a method and system for measuring the amount of medication contained within curved reservoir 20 of modular infusion pump 100. In exemplary embodiments, modular infusion pump 100 comprises a level sensing system 200 comprising two parallel resistive traces 210a (outer trace) and 210b (inner trace) on the underside of lid 121 of reservoir module 120, as illustrated in FIG. 15A. In some embodiments, resistive traces 210a and 210b comprise an electrically conductive polymeric material. In select embodiments, resistive traces 210a and 210b can be manufactured using a pad printing process. In such embodiments, pad printing is used to deposit a conductive ink on the underside of lid 121 to form the parallel resistive traces. In some other embodiments, resistive traces 210a and 210b comprise 3D circuitry formed directly on the underside of lid 121 using a molding process. In such embodiments, lid 121 is formed of a thermoplastic material. The plastic substrate (i.e., lid 121) is combined with circuit traces into a single part through selective metallization and 3D molding of the plastic material.

Figure 15B:
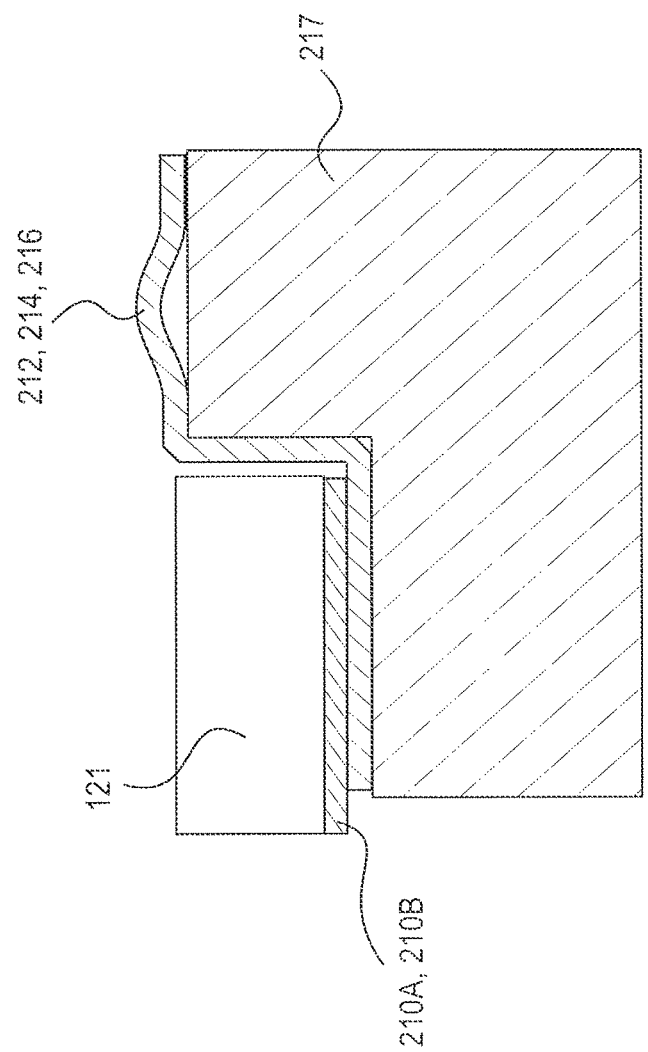
FIGS. 15B and 15C illustrate how electrical terminals of the medication level sensing system depicted in FIG. 15A make contact with the electronics in an exemplary control module.
Figure 15C:
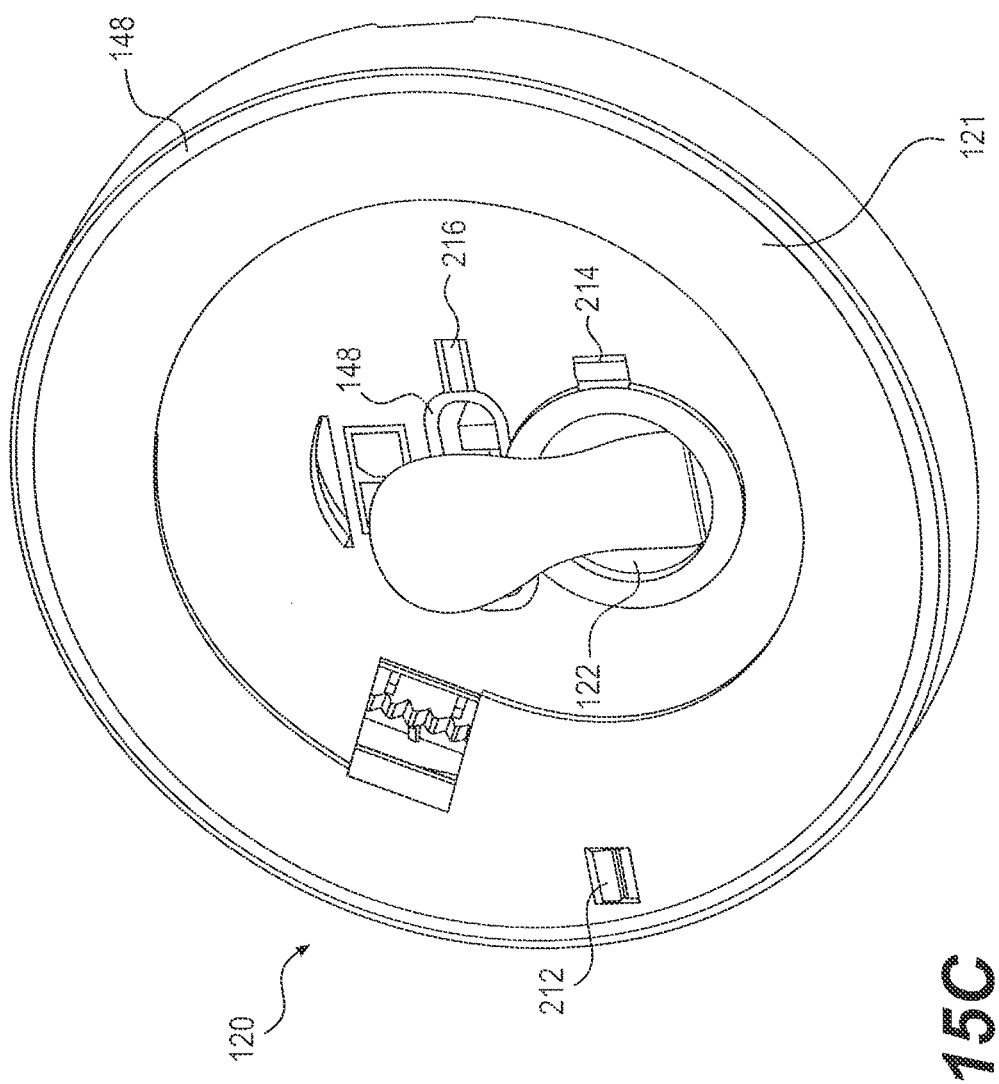

The parallel resistive traces 210a and 210b are connected to the electronics inside control module 110 via electrical terminations 212, 214, and 216. The outer trace 210a terminates at each end at terminals 212 and 216, and the inner trace 210a terminates at only one end 214. In one embodiment, terminal 216 is shared by the negative electrode (GND) of battery 122. In exemplary embodiments, electrical terminals 212, 214, and 216 are in the form of electrical spring contacts that are positioned on elevated support structures 217 formed on the base of reservoir module 120, as illustrated in FIG. 15B. The electrical spring contacts bring the resistive traces at the bottom of lid 121 to the top surface of the lid so that the electronics inside control module 110 can connect to them. FIG. 15C illustrates how the electrical contacts extend out of the top of reservoir module 120 when lid 121 is placed on it.

In exemplary embodiments, the parallel resistive traces 210a and 210b are located immediately above the feeder track 31, which contains drive train 80 in its entirety when curved reservoir 20 is completely filled with medication. As described earlier in this disclosure, and further demonstrated in FIG. 16, plunger 32 is located at the proximal end of drive train 80 and cursor 33 forms the most distal element of drive train 80. Cursor 33 and the parallel resistive traces 210a and 210b together form level sensing system 200. The purpose of cursor 33 is to provide a moving electrical short between the outer trace 210a and inner trace 210b. When curved reservoir 20 is not filled with medication, drive train 80 is located within the curved reservoir in its entirety, except for cursor 33 and segment 144 of the drive train which engages lead screw 89. When the reservoir is filled (in full or in part) with medication, drive train 80 along with cursor 33 is driven backwards into the feeder track 31, thus pushing backwards the electrical short between the resistive traces 210a and 210b. When reservoir 120 is mated with control module 110, the electronics of the control module can determine the amount of medication in the reservoir by measuring the resistance value between terminals 212, 214, and 216. As drive train 80 is driven forward by lead screw 89 to dispense medication from curved reservoir 20, cursor 33 moves forward as well under the resistive traces 210a and 210b, and thereby changes the location of the electrical short between the two resistive traces. In exemplary embodiments, the changing location of the electrical short produces different resistive values, which alters the voltage signal measured by control module 110 via electrical terminations 212, 214, and 216. The voltage signal is converted into a corresponding volume of medication present in curved reservoir 20.

Figure 16:
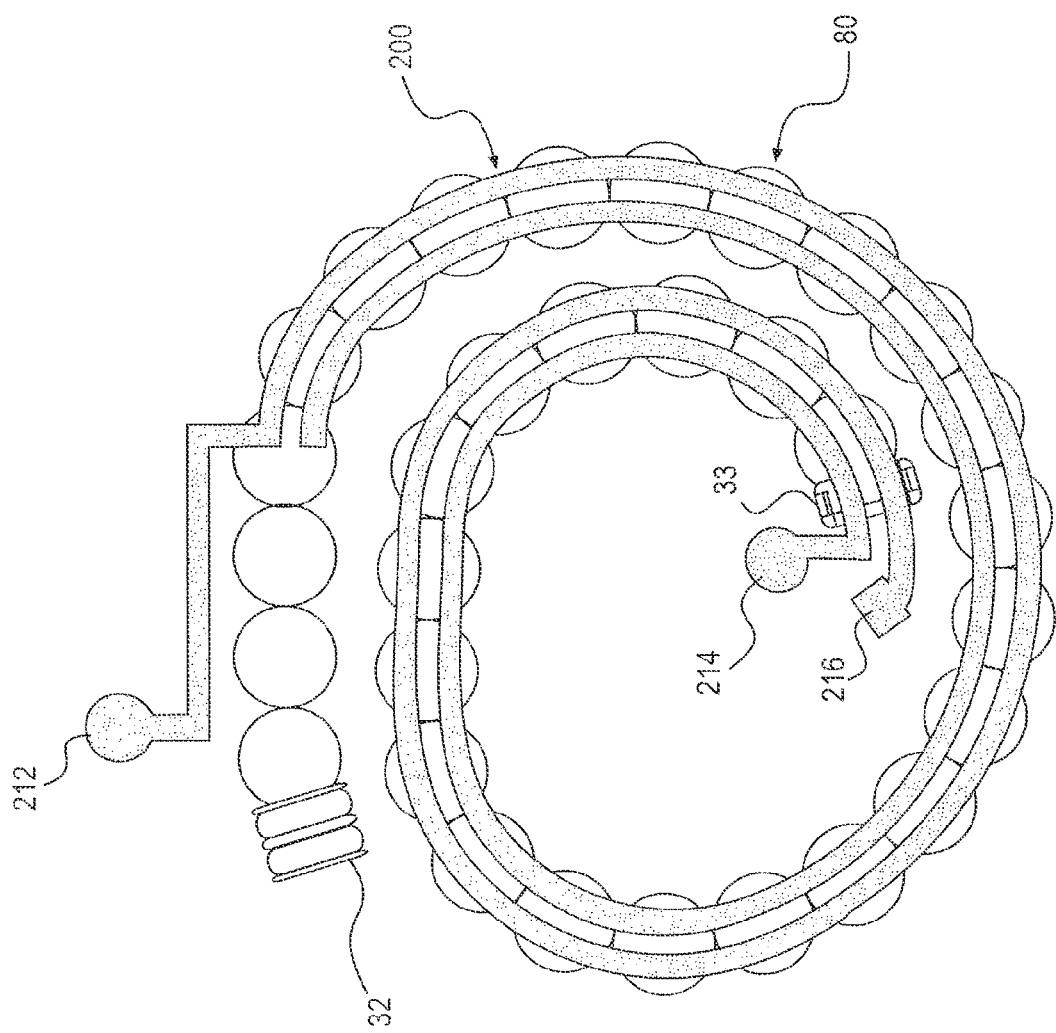
FIG. 16 illustrates a top close-up view of the medication level sensing system depicted in FIG. 15A.

Thus, level sensing system 200 functions as a potentiometer to determine the amount of medication contained within reservoir 20. In illustrative embodiments, as depicted in FIGS. 15 and 16, outer track 210a functions as the potentiometer track and the inner track 210b serves to transmit the voltage sensed by cursor 33 to control module 110 where the sensed voltage is converted into a corresponding level of medication within reservoir 20. In exemplary embodiments, level sensing system 200 can be used not only to sense the level of medication in the reservoir, but also as a safety feature to cross-check the accuracy of the medication delivery mechanism.

Figure 17B:
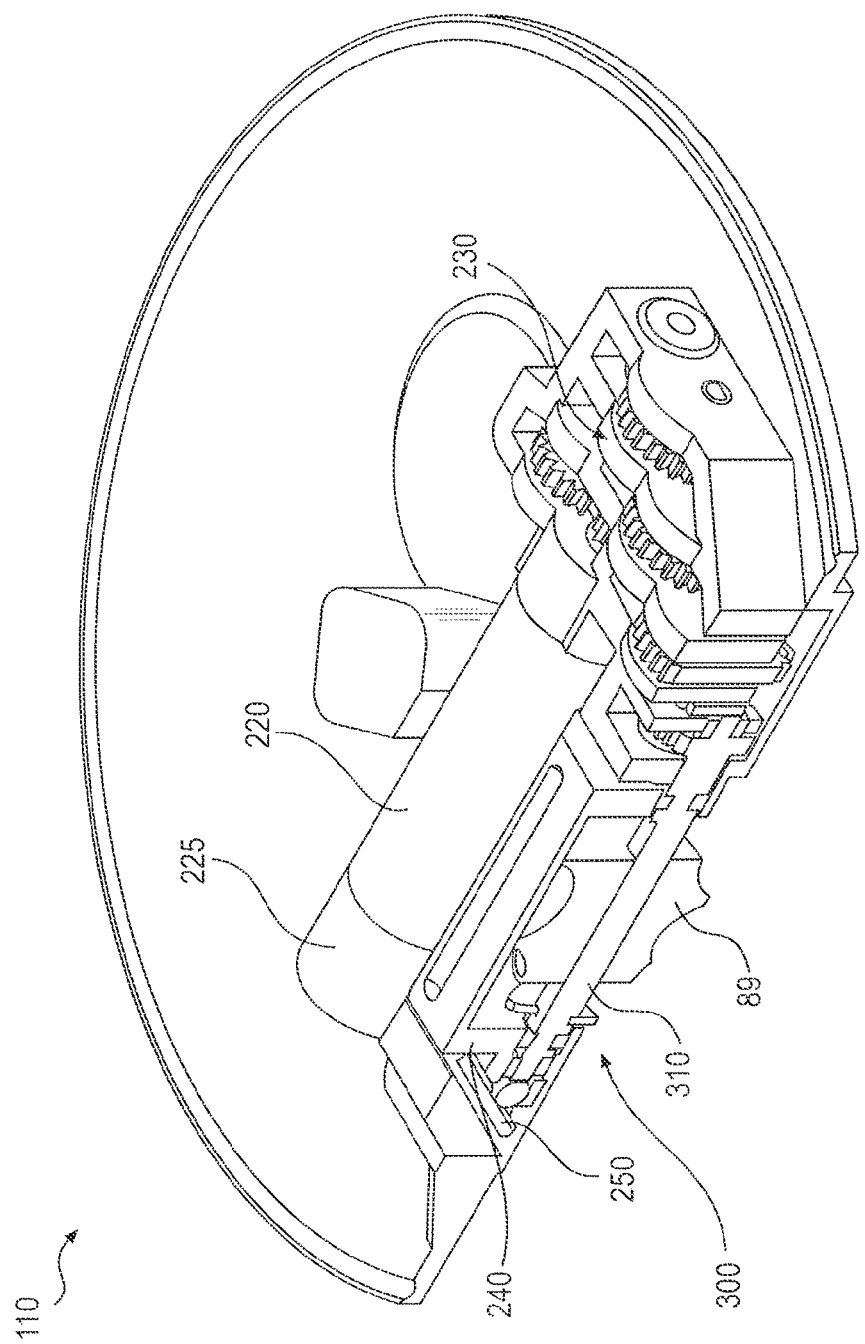

Another aspect of the present disclosure is an actuation mechanism for delivering medication from the curved reservoir 20 to a user. In exemplary embodiments of infusion pump 100, control module 110 provides mechanical actuation to reservoir module 120, which enables the reservoir module to deliver medication to a user. FIG. 17A and 17B illustrates the mechanical components of an exemplary control module 110 (with the top cover removed). As shown in FIG. 17A, control module 110 includes an electric motor 220. In some embodiments, motor 220 is coupled to a motor shaft encoder 225, which provides rotational information about the motor. An output shaft of motor 220 is coupled to a gearbox 230, which increases the torque provided by the motor. In select embodiments, motor shaft encoder 225 is mounted on any of the gears of gearbox 230 instead of being connected directly to motor 220. This helps in preserving the torque of the motor and conserve battery energy. In one such embodiment, an extra gear is added to gearbox 230 and the motor shaft encoder is mounted on the extra gear, which is mated with one of the bigger gears in gearbox 230. The output of gearbox 230 is coupled to actuation device 300, which is located under a lead screw enclosure 240 which forms part of the control module housing. An occlusion sensor 250 is connected to actuation device 300 to detect any blockage in the medication delivery path.

Figure 17C:
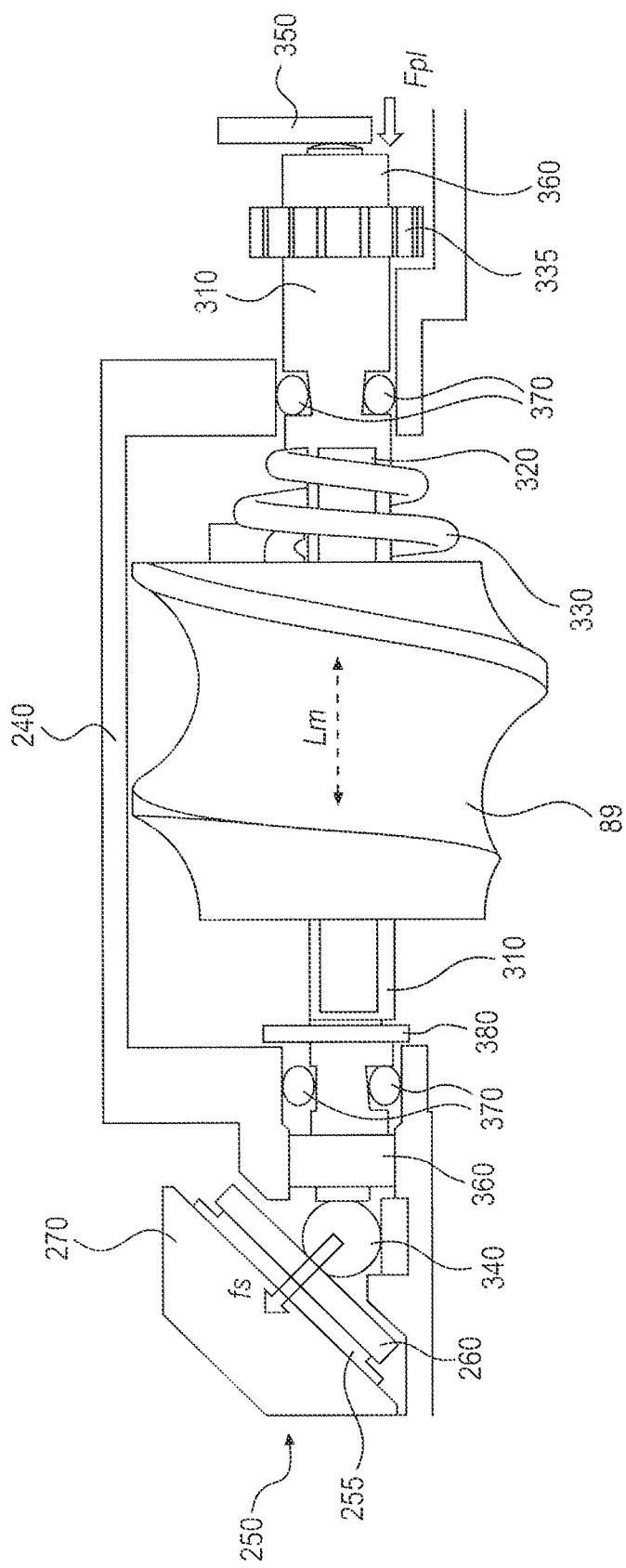

FIG. 17B shows a cross-sectional view of control module 110 providing more details on actuation device 300. FIG. 17C shows a cross-sectional view of actuation device 300. The output of gearbox 230 is mechanically coupled to a drive shaft 310, which receives rotational motion from gearbox 230. In exemplary embodiments, gear box 230 is coupled to the drive shaft via a spur gear 335.

Lead screw 89 slides on drive shaft 310 and rotates with it. In exemplary embodiments, a flat surface 320 is located on drive shaft 310 and the lead screw travels laterally along the flat surface 320, as illustrated by lateral movement Lm in FIG. 17C. A centering spring 330, which can be used in both compression and elongation, keeps lead screw 89 centered on the flat 310 of the drive shaft when control module 110 is not connected to reservoir module 120. When the control module 110 and reservoir module 120 are mated together, the ability of the spring-loaded lead screw to slide back and forth allows the lead screw to find a suitable location for its threads between the threads of drive train 80 and thus facilitate proper engagement of the lead screw and the drive train.

Referring again to FIG. 17C, drive shaft 310 is further coupled to a force sensor 255 via a ball 340. Force sensor 255 is part of the occlusion sensor 250 in the control module. Ball 340 transmits to the sensor any lateral force Fs applied to it by the rotating drive shaft. In exemplary embodiments, ball 340 is made of metal or ceramic.

A light force, which acts as a preload force Fpl, is applied on the drive shaft to keep it in contact with ball 340, and the ball in contact with force sensor 255. In exemplary embodiments, a leaf spring 350 is used to apply a light force on drive shaft 310 to ensure that no gap exists between the drive shaft and force sensor 255. Force sensor 255 continuously monitors the force on the drive shaft during operation. Any force build-up or spike in force can indicate that there is an occlusion in the medication delivery pathway and the user can be alerted to take remedial measures. In exemplary embodiments, ball 340 applies force Fs to a front plate 260, which in turn applies the force to sensor 255. The purpose of the front plate is to distribute the concentrated force applied by ball 340 over the entire surface of force sensor 255. A rigid back plate 270 ensures that force sensor 255 can measure the load without being affected by any deformation of the back plate. In exemplary embodiments, as illustrated in FIG. 17C, occlusion sensor 250, including force sensor 255, front plate 260 and back plate 270, are positioned at a 45° angle with respect to the axis of the shaft. The angled placement reduces the total height of the occlusion sensor and amplifies the force measured by force sensor 255 by a factor of 1.4142. When the lead screw reaches the "drive" position, with the "drive" position being defined as the position assumed by lead screw 89 when it transmits mechanical actuation to drive train 80 in reservoir module 120, centering spring 330 becomes elongated and the lead screw is pressed against retaining ring 380. In this position, the lateral force applied to the lead screw (when actuating the drive train) will be transmitted to force sensor 255 via a retaining ring 380 and shaft 310. In some embodiments, retaining ring 380 is snapped into a groove in drive shaft 310. The retaining ring forms a hard stop to the lateral displacement of lead screw 89 when travelling in the direction of force sensor 255.

Referring again to FIG. 17C, an exemplary occlusion mechanism 300 includes a pair of bearings 360 at each end of drive shaft 310 to support the drive shaft and allow it to rotate freely. Further, in some embodiments, occlusion mechanism 300 includes O-rings 370 at each end of drive shaft 310 to form barriers between the interior and exterior of control module 110 so as to avoid contamination of the interior of the control module.

When control module 110 and reservoir module 120 are mated together, lead screw 89 is positioned randomly on drive train 80. For instance, in the process of positioning the threads of lead screw 89 between the threads of drive train 80, the lead screw can move towards the spur gear 335 and compress centering spring 330. In such a case, a gap separates lead screw 89 from retaining ring 380. To close the gap, actuation device 300 is primed by rotating drive shaft 310. As the drive shaft rotates, lead screw moves laterally over the immobilized drive train 80 (the drive train is immobilized because the medication in the reservoir is incompressible and the medication output port is closed) towards retaining ring 380. The gap is closed when lead screw 89 makes contact with the retaining ring and the lead screw cannot move further. As rotation of drive shaft 310 continues, lead screw 89 presses against retaining ring 380 and results in a push force on drive train 80. If the medication output port (port 125/output port 125A) is open, the push force results in a forward motion of drive train 80 which leads to delivery of medication. As the push force is applied to drive train 80, a corresponding equal and opposite reaction force (under Newton's third law) is applied to ball 340, which is in turn transmits a force Fs to force sensor 255 that is proportional to the force required to move drive train 80 forward. In exemplary embodiments, the push force on drive train 80 is registered by force sensor 255, which triggers the electronics in the control module to stop rotating drive shaft 310 and to indicate to the user that the system is primed.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A modular infusion pump for dispensing a fluid, comprising:
    a reservoir module, comprising: a tubular, curved reservoir containing the fluid, the curved reservoir having a proximal end and a distal end;
    a flexible drive train configured to slidably fit within the curved reservoir and to expel the fluid through the proximal end of the reservoir, the flexible drive train including:
        a plunger at a proximal end of the drive train,
        a cursor at a distal end of the drive train,
        a flexible filament extending between the cursor and the plunger, and
        a plurality of balls positioned along and connected by the filament between the plunger and the cursor,
            wherein each of the plurality of balls includes a center through hole extending therethrough, the flexible filament extending through the center through holes of the balls, wherein each of the balls further comprises a tapered slot, wherein a diameter of the center through hole is smaller than a largest width of the tapered slot located at an outer diameter of the ball, and further wherein the diameter of the center through hole is larger than a smallest width of the tapered slot located adjacent to the center through hole; and
    a control module comprising an electric motor, a drive shaft, and a lead screw, wherein the lead screw is configured to mechanically engage the drive train when the reservoir module is connected to the control module.

2. The modular infusion pump of claim 1, wherein the reservoir module comprises a medication output port fluidly coupled to the proximal end of the reservoir.

3. The modular infusion pump of claim 2, further comprising a cradle configured to mate with the medication output port of the reservoir module.

4. The modular infusion pump of claim 3, wherein the cradle is configured to adhere directly to skin of a patient.

5. The modular infusion pump of claim 4, wherein the cradle comprises a flexible cannula configured to penetrate the skin of the patient.

6. The modular infusion pump of claim 2, further comprising an infusion set configured to mate with the medication output port.

7. The modular infusion pump of claim 6, wherein the infusion set comprises a tubing having an insertion needle at one end thereof, the insertion needle configured to deliver medication to a patient subcutaneously.

8. The modular infusion pump of claim 2, wherein the medication output port is configured to connect interchangeably with a cradle configured to adhere direct to a patient's skin, or an infusion set comprising a medication delivery tubing.

9. The modular infusion pump of claim 2, wherein the reservoir module further comprises a self-sealing fill port configured to enable loading of medication into the reservoir.

10. The modular infusion pump of claim 2, wherein the medication output port is further configured to enable loading of medication into the reservoir.

11. The modular infusion pump of claim 1, wherein the reservoir module comprises a hydrophobic vent configured to equalize pressure inside and outside the reservoir module.

12. The modular infusion pump of claim 1, wherein the reservoir module further comprises a feeder track having a continuous, curved wall structure configured to guide the drive train.

13. The modular infusion pump of claim 1, further comprising a locking mechanism configured to mate the reservoir module with the control module.

14. The modular infusion pump of claim 13, wherein the locking mechanism comprises a locking pin on the control module and latching tabs on the reservoir module, and further wherein the locking pin and the latching tabs are configured to engage together when the reservoir module and the control module are brought in contact with each other.

15. The modular infusion pump of claim 1, wherein the control module further comprises at least one gear coupled to an output shaft of the electric motor.

16. The modular infusion pump of claim 15, wherein the at least one gear is mechanically coupled to the drive shaft.

17. An infusion pump for delivering medication to a user, the pump comprising:
  a reservoir module including a tubular medication reservoir having a curved configuration, the medication reservoir comprising a medication delivery outlet at a proximal end;
  a flexible, and continuous drive train comprising:
    a plunger at a proximal end of the drive train,
    a cursor at a distal end of the drive train,
    a flexible filament extending between the cursor and the plunger, and
    a plurality of balls positioned along and connected by the filament between the plunger and the cursor,
      wherein each of the plurality of balls includes a center through hole extending therethrough, the flexible filament extending through the center through holes of the balls, wherein each of the balls further comprises a tapered slot, wherein a diameter of the center through hole is smaller than a largest width of the tapered slot located at an outer diameter of the ball, and further wherein the diameter of the center through hole is larger than a smallest width of the tapered slot located adjacent to the center through hole; and
  a control module including an actuation device configured to drive the drive train through the medication reservoir.

18. The infusion pump of claim 17, wherein the medication reservoir has a circular cross-section.

19. The infusion pump of claim 17, wherein the medication reservoir is made of a flexible polymeric material.

20. The infusion pump of claim 19, wherein the polymeric material is high density polyethylene.

21. The infusion pump of claim 17, wherein the medication reservoir is made of a rigid polymeric material.

22. The infusion pump of claim 17, wherein a length of the medication reservoir exceeds a diameter of the medication reservoir.

23. The infusion pump of claim 17, wherein the medication reservoir has at least one straight section.

24. The infusion pump of claim 17, wherein the medication reservoir is curved throughout a length of the reservoir.

25. The infusion pump of claim 17, wherein the cursor is configured to indicate the position of the drive train within the medication reservoir.

26. The infusion pump of claim 17, wherein the plunger is configured to provide a hermetic seal between the plunger and an inner surface of the medication reservoir.

27. The infusion pump of claim 17, wherein the plunger is compressible.

28. The infusion pump of claim 17, wherein the plunger comprises an elastomeric ball.

29. The infusion pump of claim 17, wherein the actuation device comprises an electric motor.

30. The infusion pump of claim 29, wherein the electric motor is mechanically coupled to a motor shaft encoder configured to sense rotation of the electric motor.

31. The infusion pump of claim 29, wherein an output shaft of the electric motor is mechanically coupled to at least one gear.

32. The infusion pump of claim 31, wherein the at least one gear is mechanically coupled to a drive shaft.

33. The infusion pump of claim 32, wherein the drive shaft is further coupled to a force sensor configured to sense lateral forces generated by rotation of the drive shaft.

34. The infusion pump of claim 32, wherein the drive shaft is adapted to mount a lead screw configured to mechanically engage the drive train.

35. The infusion pump of claim 34, wherein the drive shaft is configured to enable the lead screw to slide on the drive shaft axially and to rotate with the drive shaft.

36. The infusion pump of claim 17, wherein the filament is stretchable, the filament having an unstretched diameter larger than the smallest width of the tapered slot and smaller than the diameter of the center through hole, the filament having a stretched diameter smaller than the smallest width of the tapered slot.

* * * * *